United States Patent [19]
Gangjee

[11] Patent Number: 5,939,420
[45] Date of Patent: Aug. 17, 1999

[54] PYRROLO[2,3D]DERIVATIVES

[75] Inventor: Aleem Gangjee, Allison Park, Pa.

[73] Assignee: Duquesne University of the Holy Ghost, Pittsburgh, Pa.

[21] Appl. No.: 08/660,023

[22] Filed: Jun. 6, 1996

Related U.S. Application Data

[60] Continuation-in-part of application No. 08/515,491, Aug. 15, 1995, Pat. No. 5,736,547, which is a division of application No. 08/304,044, Sep. 12, 1994, Pat. No. 5,508,281, which is a continuation-in-part of application No. 07/950,982, Sep. 23, 1992, Pat. No. 5,346,900, which is a continuation of application No. 07/829,519, Jan. 31, 1992, abandoned, which is a continuation of application No. 07/682,043, Apr. 8, 1991, abandoned.

[51] Int. Cl.⁶ ........................ A61K 31/505; C07D 471/04
[52] U.S. Cl. ............................................ 514/258; 544/280
[58] Field of Search .............................. 544/280; 514/258

[56] References Cited

U.S. PATENT DOCUMENTS

| | | | |
|---|---|---|---|
| 3,904,624 | 9/1975 | Perronnet et al. | 260/251 P |
| 4,435,570 | 3/1984 | Nishimura et al. | 544/280 |
| 4,923,872 | 5/1990 | Kostlan et al. | 514/258 |
| 4,996,206 | 2/1991 | Taylor et al. | 514/258 |
| 5,028,608 | 7/1991 | Taylor et al. | 514/258 |
| 5,248,775 | 9/1993 | Taylor et al. | 544/280 |
| 5,254,687 | 10/1993 | Taylor et al. | 544/280 |
| 5,344,932 | 9/1994 | Taylor | 544/280 |
| 5,346,900 | 9/1994 | Gangjee | 514/258 |
| 5,508,281 | 4/1996 | Gangjee | 514/258 |

OTHER PUBLICATIONS

Hurlbert et al., "Studies on Condensed Pyrimidine Systems. XXIII. Synthesis of 2,4–Diaminopyrido[2,3–d]pyrimidines from β–Keto Esters", *J. Med. Chem.*, vol. 11, pp. 703–707 (1968).

Hurlbert et al., "Studies on Condensed Pyrimidine Systems. XXIV. The Condensation of 2,4,6–Triaminopyrimidine with Malondialdehyde Derivatives", *J. Med. Chem.*, vol. 11, pp. 708–710 (1968).

Hurlbert et al., "Studies on Condensed Pyrimidine Systems. XXV. 2,4–Diaminopyrido[2,3–d]pyrimidines. Biological Data", *J. Med. Chem.*, vol. 11, pp. 711–717 (1968).

Grivsky et al., "Synthesis and Antitumor Activity of 2,4–Diamino–6–(2,5–dimethoxybenzyl)–5–meethylpyrido[2,3–d–]pyrimidine", *J. Med. Chem.*, vol. 23, pp. 327–329 (1980).

Elslager et al., "Folate Antagonists. 20. Synthesis and Antitumor and Antimalarial Properties of Trimetrexate and Related 6–[(phenylamino)methyl]–2,4–quinazolinediamines",*J. Med. Chem.*, vol. 26, pp. 1753–1760 (1983).

Piper et al., "Syntheses and Antifolate Activity of 5–Methyl–5–deaza Analogues of Aminopterin, of Methotrexate, Folic Acid, and N¹⁰–Methylfolic Acid", *J. Med. Chem.*, vol. 29, pp. 1080–1087 (1986).

Werbel et al., "Synthesis and Antiamalarial Activity of a Series of 2,4–Diamino–6–[(N–alkylanilino)methyl] quinazolines", *J. Heterocyclic Chem.*, vol. 24, pp. 345–349 (1987).

Gangjee et al., "Classical and Nonclassical Furo[2,3–d] pyrimidines as Novel Antifolates: Synthesis and Biological Activities", *J. Med. Chem.*, vol. 37, No. 8, pp. 1169–1176 (1994).

Gangjee et al., "Novel 2,4–Diamino–5–Substituted–pyrrolo [2,3–d]pyrimidinesas Classical and Nonclassical Antifolate Inhibitors of Dihydrofolate Reductases",*J. Med. Chem.*, vol. 38, No. 12, pp. 2158–2165 (1995).

Gangjee et al., "Effect of Bridge Region Variation on Antifolate and Antitumor Activity of Classical 5–Substituted 2,4–Diaminofuro[2,3–d]pyrimidines", *J. Med. Chem.*, vol. 38, No. 19, pp. 3798–3805 (1995).

Gangjee et al., "5–Arylthio–Substituted 2–Amino–4–oxo–6–methylpyrrol[2,3–d]pyrimidine Antifolates as Thymidylate Synthase Inhibitors and Antitumor Agents", *J. Med. Chem.*, vol. 38, No. 22, pp. 4495–4502 (1995).

*Primary Examiner*—Richard L. Raymond
*Assistant Examiner*—Pavanaram K Sripada
*Attorney, Agent, or Firm*—Diane R. Meyers; Arnold B. Silverman; Eckert Seamans Cherin & Mellott, LLC

[57] ABSTRACT

Pyrrolo[2,3-d]pyrimidine derivatives, and pharmaceutical acceptable salts thereof, useful in therapeutically and/or prophylactically treating patients with an illness are disclosed.

23 Claims, 9 Drawing Sheets

1: R=3',4',5' -(OCH₃)₃
2: R=3',4' -(OCH₃)₂
3: R=4' -(OCH₃)
4: R=2',5' -(OCH₃)₂
5: R=2',5' -(OC₂H₅)₂
6: R=3',4'-(Cl)₂
7: R=2',3' -(CH)₄
8: R=H (A): Raney Ni/HCOOH; (B): NaBH$_3$; (C): 30% HBr-AcOH; (D): DMF; (E): NaH/DMF

51

R₁ = H: R₂ =
51a : 2', 5' - (OCH₃)₂
51b : 3', 4' - (Cl)₂
51c : 2', 3' - (CH)₄

R₁ = CH₃: R₂ =
52 : 2', 5' - (OCH₃)₂
53 : 3', 4' - (Cl)₂
54 : 2', 3' - (CH)₄

R =
55 : 3', 4' - (OCH₃)₂
56 : 3', 4' - (Cl)₂
57 : 2', 3' - (CH)₄
58 : 3', 4' - (CH)₄

R =
59 : H
60 : CH₃

PYRROLO[2,3D]DERIVATIVES

This is a continuation-in-part application of U.S. application Ser. No. 08/515,491 filed Aug. 15, 1995 now U.S. Pat. No. 5,736,547, which is a divisional of U.S. application Ser. No. 08/304,044, filed on Sep. 12, 1994 now U.S. Pat. No. 5,508,281, which is a continuation-in-part of U.S. application Ser. No. 07/950,982 filed Sep. 23, 1992, now U.S. Pat. No. 5,346,900, which is a continuation of U.S. application Ser. No. 07/829,519 filed Jan. 31, 1992, now abandoned, which in turn is a continuation of U.S. application Ser. No. 07/682,043 filed Apr. 8, 1991, now abandoned.

The invention described herein was made in the course of work supported in part by the National Institutes of General Medical Sciences, Grant No. 1-RO1-GM-40998 from the National Institutes of Health, U.S. Department of Health and Human Services. The Government has certain rights in this invention.

BACKGROUND OF THE INVENTION

1. Field of the Invention

This invention relates to pyrimidine derivative compounds and pharmaceutically acceptable salts thereof. More specifically, this invention relates to furo[2,3-d]pyrimidines, pyrrolo[2,3-d]pyrimidines, pyrrolo[3,2-d]pyrimidines, pyrrolo[3,4-d]pyrimidines, thieno[2,3-d]pyrimidines, cyclopentapyrimidines and cyclopenta[d]pyrimidines. These compounds have been found useful in resisting and treating *Pneumocystis carinii* and *Toxoplasmosis gondii* infections in immunocompromised patients, such as, for example, patients with autoimmune deficiency syndrome (AIDS). These compounds are also useful as potential antitumor, antibiotic, antimalarial, antifungal or antiprotozoal agents, or as synergistic agents when used with sulfonamides may require the use of leucovorin rescue. These compounds are also useful as antitumor agents in cancer patients. Methods of preparing and using these compounds are also provided.

2. Description of the Background Art

Various pyrimidine systems, such as the pyrido[2,3-d] pyrimidine ring system, have been studied due to their involvement in the inhibition of dihydrofolate reductase (DHFR) enzymes activity. The pyrimidine derivatives disclosed herein function as DHFR inhibitors. Because DHFR reduces dihydrofolate to tetrahydrofolate, inhibition of DHFR deprives the cell of tetrahydrofolate, without which the cell cannot produce 5,10-Methylenetetrahydrofolate. 5,10-Methylenetetrahydrofolate is essential for cell growth. The inhibition of DHFR by the compounds, and pharmaceutically acceptable salts thereof, of this invention results in the inhibition of DNA synthesis and leads to cell death. Methotrexate (MTX), trimetrexate (TMQ), piritrexim (PTX) and other folic acid analogues function as inhibitors of cell growth by similar mechanisms involving the inhibition of dihydrofolate reductase.

The pyrimidine derivatives disclosed herein further function as thymidylate synthase (TS) inhibitors. TS, along with DHFR, forms part of the systems responsible for the synthesis of deoxythymidylate (dTMP) from deoxyuridylate (dUMP). TS catalyzes the sole de novo synthesis of dTMP from dUMP. Inhibition of TS, therefore, deprives the cell of thymidine, which is an essential constituent of DNA. Typically, the compounds as described herein where X and Y are both $NH_2$ will function as DHFR inhibitors, and compounds where X is OH and Y is $NH_2$ will function as TS inhibitors.

Drugs useful for the reduction of cancerous cells are also known.

Elslager, Edward F., et al., "Folate Antagonists. 20. Synthesis and Antitumor and Antimalarial Properties of Trimetrexate and Related 6-[(Phenylamino)methyl]-2,4-quinazolinediamines" *J. Med. Chem.*, Vol. 26 pp. 1753–1760 (1983)), discloses the preparation of quinazolinediamines. This article states that the quinazolinediamines exhibit potent antimalarial, antibacterial and antitumor activity.

Methods of synthesizing diaminopyrido[2,3-d] pyrimidines having various substituents are known. See Hurlbert, B. S., et al., "Studies on Condensed Pyrimidine Systems. XXIII. Synthesis of 2,4-Diaminopyrido[2,3-d] pyrimidines from β-Keto Esters", *J. Med. Chem.*, Vol. 11, pp. 703–707 (1968), and Hurlbert, B. S., and Valenti, B. F., "Studies on Condensed Pyrimidine Systems. XXIV. The Condensation of 2,4,6-Triaminopyridimine with Malondialdehyde Derivatives", *J. Med. Chem.*, Vol. 11, pp. 708–710 (1968).

Hurlbert, B. S., et al., "Studies on Condensed Pyrimidine Systems. XXV. 2,4-Diaminopyrido[2,3-d]pyrimidines. Biological Data", *J. Med. Chem.*, Vol. 11, pp. 711–717 (1968), discloses the antimicrobial activities of several subgroups of pyridopyrimidines. This article states that 2,4-diaminopyrido[2,3-d]pyrimidines bearing alkyl and aralkyl substituents in the pyrimidine moiety are inhibitors of dihydrofolate reductase having antibacterial and antiprotozoal activity and that these compounds potentiate sulfonamides.

Grivsky, E. M., et al., "Synthesis and Antitumor Activity of 2,4-Diamino-6-(2,5-dimethoxybenzyl)-5-methylpyrido [2,3-d]pyridimine", *J. Med. Chem.*, Vol. 23, pp. 327–329 (1980), discloses the synthesis of 2,4-diamino-6-(2,5-dimethoxybenzyl)-5-methylpyrido[2,3-d]pyridimine (BW301U,7). This article states that BW301U,7 is as effective as methotrexate as an inhibitor of dihydrofolate reductase purified from human leukemic cells and, in contrast to metoprine, has minimal activity as an inhibitor of histamine metabolism.

Werbel, Leslie, M., et al., "Synthesis and Antimalarial Activity of a Series of 2,4-Diamino-6-[(N-alkylanilino) methyl]quinazolines [1,2]", *J. Heterocyclic Chem.*, Vol. 24, pp. 345–349 (1987), discloses the synthesis of N6 substituted quinazoline dihydrofolate reductase inhibitors. This article states that these analogs demonstrate substantial activity against *Plasmodium berghei* infections in mice.

Piper, J. R., et al., "Syntheses and Antifolate Activity of 5-Methyl-5-deaza Analogues of Aminopterin, Methotrexate, Folic Acid, and $N^{10}$-Methylfolic Acid", *J. Med. Chem.*, Vol. 29, pp. 1080–1087 (1986), discloses that 5-methyl-5-deaza analogues of aminopterin and methotrexate are much more growth inhibitory than methotrexate.

Pyrido [2,3-d] and [3,2-d] pyrimidines are also disclosed in U.S. Pat. Nos. 5,346,900 and 5,508,281, and co-pending application Ser. No. 08/515,491, all of which are hereby expressly incorporated by reference.

Pyrrolo[2,3-d]pyrimidines are disclosed by Gangjee et al. in "Novel 2,4-diamino-5-substituted-pyrrolo[2,3-d] pyrimidines As Classical and Non-Classical Antifolate Inhibitors of Dihydrofolate Reductases", *J. Med. Chem.*, Vol. 38, pp. 2158–2165 (Jun. 6, 1995).

Gangjee, A., et al., "Classical and Non-Classical Furo[2, 3-d]Pyrimidines As Novel Antifolates: Synthesis and Biological Activities", *J. Med. Chem.*, Vol. 37, pp. 1169–1176 (1994), discloses the furo[2,3-d]pyrimidines.

In spite of the art discussed above, there remains a very real and substantial need for compounds that are more active and more selective than known compounds at resisting and treating infections caused by *Pneumocystis carinii* and *Toxoplasmosis gondii* in immunocompromised patients, reducing the tumor size and/or the number of cancerous cells in cancer patients, and for methods of preparing and using such compounds.

SUMMARY OF THE INVENTION

The present invention has met the above described need. The present invention provides pyrrolo[2,3-d]pyrimidine compounds, and pharmaceutically acceptable salts thereof, having the formula (1):

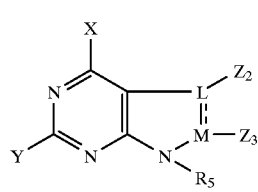

(1)

wherein X and Y are the same or different and are selected from the group consisting of OH and $NH_2$;

wherein L and M are selected from the group consisting of carbon and CH, the chemical bond between L and M is selected from the group consisting of a single bond and a double bond, L and M are carbon when the bond is a double bond, and L and M are CH when the bond is a single bond;

wherein $Z_2$ and $Z_3$ are different and are selected from the group consisting of $R_4$ and

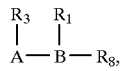

where $Z_2$ is $R_4$ when $Z_3$ is

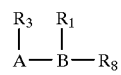

and $Z_2$ is

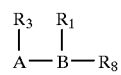

when $Z_3$ is $R_4$;

wherein A is selected from the group consisting of CH and zero;

wherein B is selected from the group consisting of CH, nitrogen, N—$CH_2$, $CH_2$—N, $CH_2$—$CH_2$, oxygen and sulfur;

wherein $R_1$ is selected from the group consisting of hydrogen, a lower alkyl group, a nitroso group, a formyl group and zero and $R_1$ is zero when B is oxygen or sulfur;

wherein $R_3$ is selected from the group consisting of hydrogen, a lower alkyl group and zero, and $R_3$ is zero when A is zero;

wherein $R_4$ is selected from the group consisting of hydrogen and a lower alkyl group;

wherein $R_5$ is selected from the group consisting of hydrogen and a lower alkyl group;

wherein $R_8$ is selected from the group consisting of naphthyl, mono-, di- and tri-substituted naphthyl, thionaphthyl, thiophenyl and hydroxyphenyl when $R_1$ is hydrogen and $R_4$ is hydrogen;

wherein $R_8$ is selected from the group consisting of phenyl, mono-, di- and tri-substituted phenyl, naphthyl, mono-, di- and tri-substituted naphthyl, pyridine and p-aroyl-L-glutamate when $R_1$ is a lower alkyl group and $R_4$ is hydrogen;

wherein $R_8$ is selected from the group consisting of pyridine, phenyl, mono-, di- and tri-substituted phenyl, naphthyl, and mono-, di- and tri-substituted naphthyl and p-aroyl-L-glutamate when $R_1$ is zero;

wherein $R_8$ is selected from the group consisting of phenyl, mono-, di- and tri-substituted phenyl, naphthyl, mono-, di- and tri-substituted naphthyl and p-aroyl-L-glutamate when $R_1$ is hydrogen and $R_4$ is a lower alkyl group; and wherein $R_8$ is not p-benzoyl-L-glutamate or pyridine when X is OH, A is zero, B is sulfur, $R_4$ is methyl and $R_5$ is hydrogen, and $R_8$ is not p-benzoyl-L-glutamate when X is OH, A is CH, B is CH, $R_4$ is hydrogen and $R_5$ is hydrogen; and wherein each lower alkyl group is independently selected from the group consisting of lower alkyl groups having from 1 to 6 carbons.

The present invention also provides methods of synthesizing pyrrolo-[2,3-d]pyrimidine compounds, and pharmaceutically acceptable salts thereof, having the formula (2):

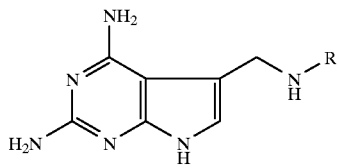

(2)

wherein R is selected from the group consisting of a lower alkyl group, a p-aroyl-L-glutamate group, an aryl group, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, alkyltriaryl group is the same or different and is selected from the group consisting of a lower alkyl group, an alkoxy, a substituted alkoxyaryloxy group and a halogen; and wherein each lower alkyl group is independently selected from the group consisting of lower alkyl groups having from about 1 to 6 carbons, comprising the steps of:

a) debrominating a pyrrole;
b) fusing the product of step a) with an amidine;
c) condensing the product of step b) with a nucleophile;
d) reducing the product of step c); and
e) purifying the compounds of step d).

The present invention also provides furo[2,3-d] pyrimidine compounds, and pharmaceutically acceptable salts thereof, having the formula (4):

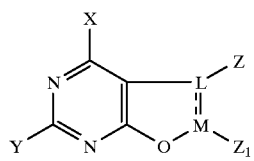

(4)

wherein X and Y are the same or different and are selected from the group consisting of OH and $NH_2$;

wherein L and M are selected from the group consisting of carbon and CH, the chemical bond between L and M is selected from the group consisting of a single bond and a double bond, L and M are carbon when the bond is a double bond, and L and M are CH when the bond is a single bond;

wherein Z and $Z_1$ are different and are selected from the group consisting of $R_4$ and

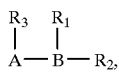

where Z is $R_4$ when $Z_1$ is

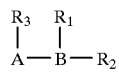

and Z is

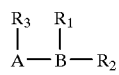

when $Z_1$ is $R_4$;

wherein A is selected from the group consisting of CH and zero;

wherein B is selected from the group consisting of sulfur, nitrogen, oxygen, CH, N—$CH_2$, $CH_2$—N, $CH_2$—$CH_2$, and zero;

wherein $R_1$ is selected from the group consisting of hydrogen, a lower alkyl group, a nitroso group, a formyl group and zero and $R_1$ is zero when B is sulfur, oxygen or zero;

wherein $R_2$ is selected from the group consisting of a lower alkyl group, p-aroyl-L-glutamate, an aryl group, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, alkyltriaryl group is the same or different and is selected from the group consisting of a lower alkyl, an alkoxy, an alkoxyaryloxy group, a halogen and zero but $R_2$ is not 3,4,5-trimethoxyphenyl, 3,4,5-trichlorophenyl, 3,4-dichlorophenyl, 2,5-dimethoxyphenyl or a p-benzoyl-L-glutamate when $R_1$ is hydrogen and $R_4$ is hydrogen, and $R_2$ is not p-benzoyl-L-glutamate when $R_1$ is methyl;

wherein $R_3$ is selected from the group consisting of hydrogen, a lower alkyl group, and zero and $R_3$ is zero when A is zero;

wherein $R_4$ is selected from the group consisting of hydrogen, a lower alkyl group and S—$R_7$ where $R_7$ is selected from the group consisting of phenyl, mono-, di- and tri-substituted phenyl, naphthyl, mono-, di- and tri-substituted naphthyl and p-aroyl-L-glutamate; and wherein each lower alkyl group is independently selected from the group consisting of lower alkyl groups having from 1 to 6 carbons.

The present invention also provides thieno[2,3-d] pyrimidine compounds, and pharmaceutically acceptable salts thereof, having the formula (5):

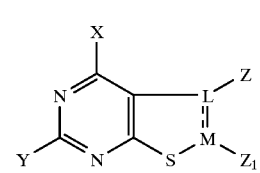

(5)

wherein X and Y are the same or different and are selected from the group consisting of OH and $NH_2$;

wherein L and M are selected from the group consisting of carbon and CH, the chemical bond between L and M is selected from the group consisting of a single bond and a double bond, L and M are carbon when the bond is a double bond, and L and M are CH when the bond is a single bond;

wherein Z and $Z_1$ are different and are selected from the group consisting of $R_4$ and

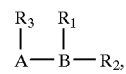

where Z is $R_4$ when $Z_1$ is

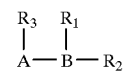

and Z is

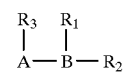

when $Z_1$ is $R_4$;

wherein A is selected from the group consisting of CH and zero;

wherein B is selected from the group consisting of sulfur, nitrogen, oxygen, CH, N—$CH_2$, $CH_2$—N, $CH_2$—$CH_2$, and zero;

wherein $R_1$ is selected from the group consisting of hydrogen, a lower alkyl group, a nitroso group, a formyl group and zero and $R_1$ is zero when B is sulfur, oxygen or zero;

wherein $R_2$ is selected from the group consisting of a lower alkyl group, an aryl group, p-aroyl-L-glutamate, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, alkyltriaryl group is the same or different and is selected from the group consisting of a lower alkyl group, an alkoxy, an alkoxyaryloxy group, a halogen and zero;

wherein $R_3$ is selected from the group consisting of hydrogen, a lower alkyl group and zero, and $R_3$ is zero when A is zero;

wherein $R_4$ is selected from the group consisting of hydrogen and lower alkyl group; and wherein each lower alkyl group is independently selected from the group consisting of lower alkyl groups having from about 1 to 6 carbons.

The present invention also provides pyrrolo[3,2-d] pyrimidine compounds, and pharmaceutically acceptable salts thereof, having the formula (6):

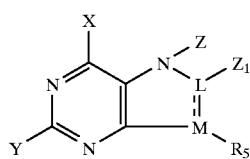

(6)

wherein X and Y are the same or different and are selected from the group consisting of OH and $NH_2$;

wherein L and M are selected from the group consisting of carbon and CH, the chemical bond between L and M is selected from the group consisting of a single bond and a double bond, L and M are carbon when the bond is a double bond, and L and M are CH when the bond is a single bond;

wherein Z and $Z_1$ are different and are selected from the group consisting of $R_4$ and

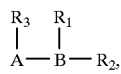

where Z is $R_4$ when $Z_1$ is

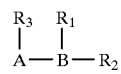

and Z is

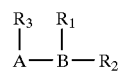

when $Z_1$ is $R_4$;

wherein A is selected from the group consisting of CH and zero;

wherein B is selected from the group consisting of sulfur, nitrogen, oxygen, CH, N—$CH_2$, $CH_2$—N, $CH_2$—$CH_2$, and zero;

wherein $R_1$ is selected from the group consisting of hydrogen, a lower alkyl group, a nitroso group, a formyl group and zero, and $R_1$ is zero when B is sulfur, oxygen or zero;

wherein $R_2$ is selected from the group consisting of a lower alkyl group, p-aroyl-L-glutamate, an aryl group, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, or alkyltriaryl group is the same or different and is selected from the group consisting of a lower alkyl group, an alkoxy, an alkoxyaryloxy group, a halogen and zero;

wherein $R_3$ is selected from the group consisting of hydrogen, a lower alkyl group and zero, and $R_3$ is zero when A is zero;

wherein $R_4$ is selected from the group consisting of hydrogen and lower alkyl group;

wherein $R_5$ is selected from the group consisting of hydrogen and lower alkyl group; and wherein each lower alkyl group is independently selected from the group consisting of lower alkyl groups having from about 1 to 6 carbons.

The present invention also provides pyrrolo[3,4-d] pyrimidine compounds, and pharmaceutically acceptable salts thereof, having the formula (7):

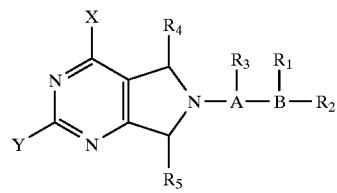

(7)

wherein X and Y are the same or different and are selected from the group consisting of OH and $NH_2$;

wherein A is selected from the group consisting of CH and zero;

wherein B is selected from the group consisting of sulfur, nitrogen, oxygen, CH, N—$CH_2$, $CH_2$—N, $CH_2$—$CH_2$, and zero;

wherein $R_1$ is selected from the group consisting of hydrogen, a lower alkyl group, a nitroso group, a formyl group and zero and $R_1$ is zero when B is sulfur, oxygen or zero;

wherein $R_2$ is selected from the group consisting of a lower alkyl group, p-aroyl-L-glutamate, an aryl group, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, or alkyltriaryl group is the same or different and is selected from the group consisting of a lower alkyl group, an alkoxy, an alkoxyaryloxy group, a halogen and zero;

wherein $R_3$ is selected from the group consisting of hydrogen, a lower alkyl group, and zero, and $R_3$ is zero when A is zero;

wherein $R_4$ is selected from the group consisting of hydrogen and lower alkyl group; and wherein each lower alkyl group is independently selected from the group consisting of lower alkyl groups having from about 1 to 6 carbons.

The present invention also provides cyclopentapyrimidine and cyclopenta[d]pyrimidine compounds, and pharmaceutically acceptable salts thereof, having the formula (8):

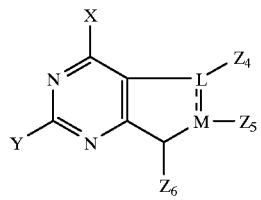

(8)

wherein X and Y are the same or different and are selected from the group consisting of OH and $NH_2$;

wherein L and M are selected from the group consisting of carbon and CH, the chemical bond between L and M is selected from the group consisting of a single bond and a double bond, L and M are carbon when the bond is a double bond, and L and M are CH when the bond is a single bond;

wherein $Z_4$, $Z_5$ and $Z_6$ are different and are selected from the group consisting of $R_4$, $R_5$ and

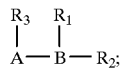

wherein A is selected from the group consisting of CH, sulfur and zero;

wherein B is selected from the group consisting of sulfur, nitrogen, oxygen, CH, $N-CH_2$, $CH_2-N$, $CH_2-CH_2$, and zero;

wherein $R_1$ is selected from the group consisting of hydrogen, a lower alkyl group, a nitroso group, a formyl group and zero, and $R_1$ is zero when B is sulfur, oxygen or zero;

wherein $R_2$ is selected from the group consisting of a lower alkyl group, p-aroyl-L-glutamate, an aryl group, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, or alkyltriaryl group is the same or different and is selected from the group consisting of a lower alkyl group, an alkyl group, an alkoxy, an alkoxyaryloxy group, a halogen and zero;

wherein $R_3$ is selected from the group consisting of hydrogen, a lower alkyl group and zero, and $R_3$ is zero when A is zero;

wherein $R_4$ is selected from the group consisting of hydrogen and a lower alkyl group;

wherein $R_5$ is selected from the group consisting of hydrogen and a lower alkyl group;

where $R_4$ is the same or different than $R_5$;

wherein each of said $R_4$, $R_5$ and

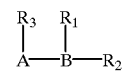

substituents is used once; and wherein each lower alkyl group is independently selected from the group consisting of lower alkyl groups having from about 1 to 6 carbons.

Methods of synthesizing the above compounds are also disclosed.

As used herein, the term "pharmaceutically acceptable salts" includes, but is not limited to, acetate, formate, glucuronate, ethantate, sulfonate, or other salts known to those skilled in the art.

In formulas 1 and 4–9, when X and Y are the same or different and are selected from the group consisting of OH and $NH_2$ groups, the enol form of the compounds is represented. The enol form is equivalent to and includes the keto form of the compounds.

As used herein, the term "lower alkyl group" refers to an alkyl group having between 1 and 6 carbons. The number of carbons in each lower alkyl group in each of formulas 1–9 can vary. For example, with reference to Formula 4, $R_1$ could represent a lower alkyl group having 1 carbon, $R_2$ could represent a lower alkyl group having 2 carbons, $R_3$ could represent a lower alkyl group having 3 carbons, and $R_4$ could represent a lower alkyl group having 4 carbons.

As will be understood one skilled in the art, when any of the variables used herein equal zero, that variable is not present in a particular embodiment of the general formula. In any of the above described formulas, when A equals zero, $R_3$ also equals zero, and B is either zero or is attached directly to L. When B is zero, $R_1$ also equals zero, and $R_2$ and $R_8$ are either zero or are attached directly to A. When both A and B are zero, $R_1$ and $R_3$ are also zero and $R_2$ and $R_8$ are either zero or is attached directly to L.

As used herein, the term aroyl, such as for example when used within the term p-aroyl-L-glutamate, refers to heteroaroyl, benzoyl, napthoyl, thiophenoyl, furophenoyl, pyrroyl, and any other aroyl as that term would be understood by one skilled in the art.

This invention also provides methods for therapeutically and/or prophylactically using the compounds, and pharmaceutically acceptable salts thereof, described herein.

This invention provides a method of using the pyrimidine derivatives of Formulas 1, 2 and 4–9 described herein for therapeutic and prophylactic purposes including employing these compounds to resist and treat secondary infections caused by *Pneumocystis carinii* and *Toxoplasmosis gondii* or other organisms in immunocompromised patients, such as for example patients with AIDS. The immunocompromised patient has a primary infection caused by a retrovirus, including for example, human immunodeficiency virus (HIV). In addition, this invention provides methods of using pyrimidine derivatives as antitumor, antibiotic, antimalarial, antifungal and antiprotozoal agents and as synergistic agents with sulfonamides in such patients.

This invention also provides methods of using pyrimidine derivatives for therapeutic purposes as antitumor agents or to otherwise destroy cancerous cells in cancer patients.

It is an object of this invention to provide pyrimidine derivative compounds, and pharmaceutically acceptable salts thereof, for substantially inhibiting dihydrofolate reductase enzymes.

It is an object of this invention to provide pyrimidine derivative compounds, and pharmaceutically acceptable salts thereof, for substantially inhibiting thymidylate synthase enzymes.

It is an object of the present invention to provide pyrimidine derivative compounds, and pharmaceutically acceptable salts thereof, having antitumor, antibiotic, antimalarial, antifungal or antiprotozoal activity or synergistic activity with sulfonamides.

It is a further object of this invention to provide pyrimidine derivative compounds, and pharmaceutically acceptable salts thereof, having effective activity against secondary infections, such as for example infections caused by *Pneumocystis carinii* and *Toxoplasmosis gondii* that occur in immunocompromised patients, such as for example patients with AIDS.

It is another object of this invention to provide pyrimidine derivative compounds, and pharmaceutically acceptable salts thereof, having effective activity against tumors and other cancerous cells, such as those caused by cancer.

It is an object of this invention to provide a method of synthesizing various pyrimidine derivative compounds, and pharmaceutically acceptable salts thereof.

It is a further object of this invention to provide methods of using in a patient a therapeutically effective amount of pyrimidine derivative compounds, or pharmaceutically acceptable salts thereof.

It is a further object of this invention to provide methods of using in a patient a prophylactically effective amount of pyrimidine derivative compounds, or pharmaceutically acceptable salts thereof.

These and other objects of the invention will be more fully understood from the drawing and the following description of the invention and the claims appended hereto.

DESCRIPTION OF THE PREFERRED EMBODIMENT

Figure 1:
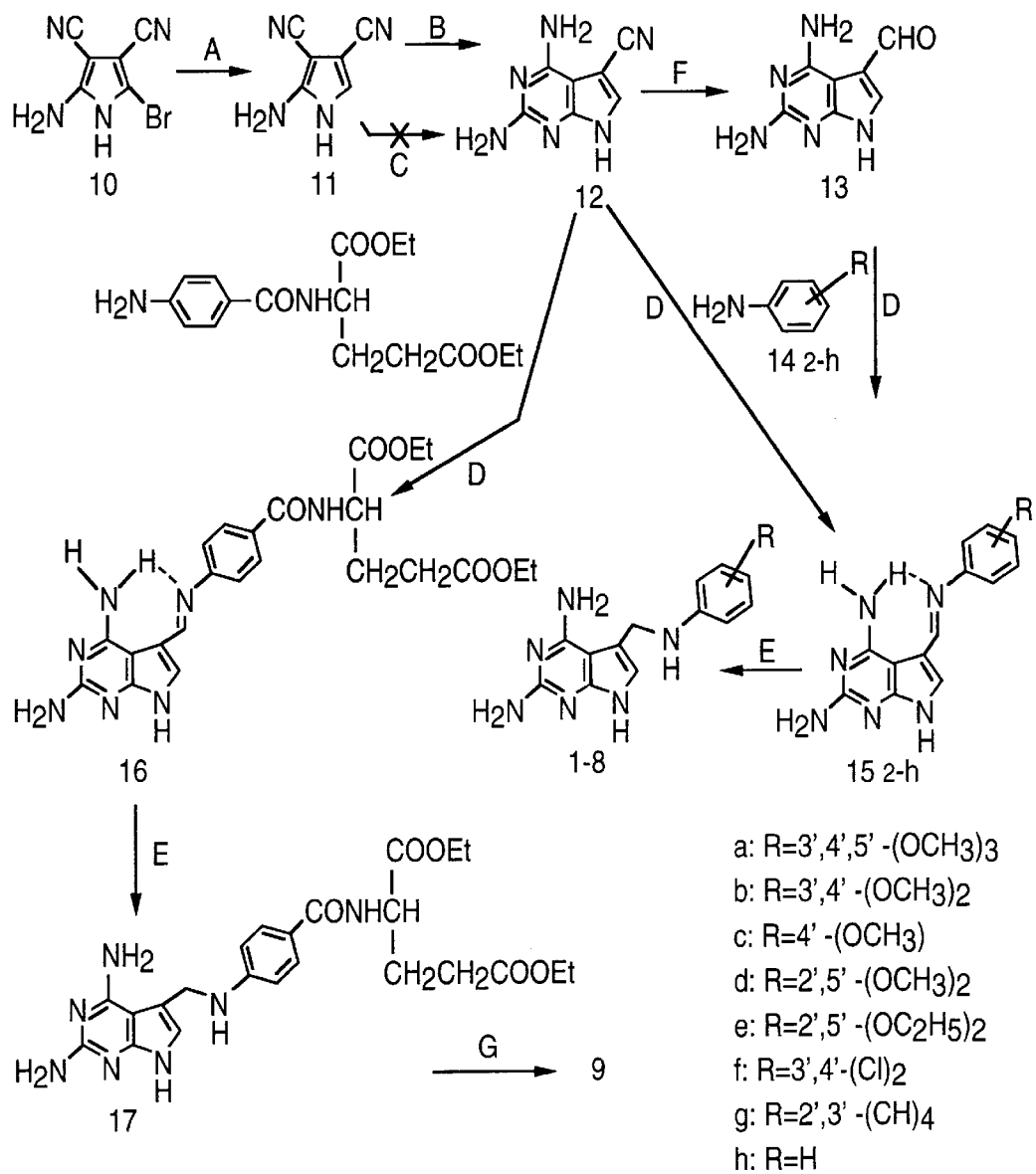
FIG. 1 shows a schematic diagram of methods of preparing 2,4-diamino-5-substituted-pyrrolo[2,3-d]pyrimidines.

As used herein, the term "patients" means members of the animal kingdom including but not limited to human beings.

The pyrimidine derivative compounds, and pharmaceutically acceptable salts thereof, and methods of preparing and using the compounds of this invention provide for the therapeutic and prophylactic treatment of secondary infections caused by *Pneumocystis carinii* and *Toxoplasmosis gondii* in immunocompromised patients. The patients have a primary infection caused by a retrovirus including human immunodeficiency virus (HIV). As will be appreciated by one skilled in the art, embodiments of the compounds, and pharmaceutically acceptable salts thereof, of the present invention which contain benzoyl-L-glutamate groups will not be applicable to these methods. That is because *Pneumocystis carinii* and *Toxoplasmosis gondii* are not generally known to take up enough of the benzoyl-L-glutamate forms of these compounds to be effective.

In addition, these compounds function as antitumor, antibiotic, antifungal, antimalarial and antiprotozoal agents, and as synergistic agents with sulfonamides.

In addition, the compounds of this invention provide for the therapeutic treatment of tumors, or other cancerous cells, in cancer patients. As used herein, the term "cancer" refers to any type of cancer including, but not limited to, leukemia, lung cancer, colon cancer, CNS cancer, melanoma, ovarian cancer, renal cancer, prostate cancer, and breast cancer.

The compounds disclosed in the present invention can all be generally described as antifolates. The pyrrolo[2,3-d] pyrimidine compounds, furo[2,3-d]pyrimidine compounds, pyrrolo[3,2-d] and pyrrolo[3,4-d]pyrimidine compounds, thieno[2,3-d]pyrimidine compounds, cyclopentapyrimidine compounds and cyclopenta[d]pyrimidine compounds, and pharmaceutically acceptable salts thereof, of this invention inhibit dihydrofolate reductase (DHFR) enzymes. The DHFR enzymes are needed for normal cell growth because they reduce dihydrofolate to tetrahydrofolate. Tetrahydrofolate is a precursor of 5,10-methylenetetrahydrofolate, which is essential for DNA replication and thus cell growth. The derivatives of the present invention inhibit dihydrofolate reductase and consequently inhibit DNA synthesis. Inhibition of DNA synthesis results in cell death.

In addition, the pyrimidine derivative compounds of the present invention, and pharmaceutically acceptable salts thereof, inhibit thymidylate synthase (TS). TS, along with DHFR, forms part of the system responsible for the synthesis of deoxythymidylate (dTMP) from deoxyuridylate (dUMP). Inhibition of TS deprives the cell of thymidine, which is an essential component of DNA.

The pyrrolo[2,3-d]pyrimidine compounds, and pharmaceutically acceptable salts thereof, of the present invention have the general formula (1):

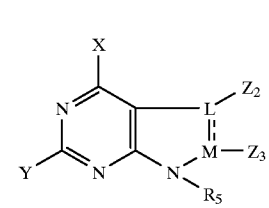

(1)

wherein X and the group same or different and are selected from the group consisting of OH and $NH_2$;

wherein L and M are selected from the group consisting of carbon and CH, the chemical bond between L and M is selected from the group consisting of a single bond and a double bond, L and M are carbon when the bond is a double bond, and L and M are CH when the bond is a single bond;

wherein $Z_2$ and $Z_3$ are different and are selected from the group consisting of $R_4$ and

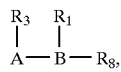

where $Z_2$ is $R_4$ when $Z_3$ is

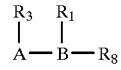

and $Z_2$ is

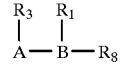

when $Z_3$ is $R_4$;

wherein A is selected from the group consisting of CH and zero;

wherein B is selected from the group consisting of CH, nitrogen, N—CH$_2$, CH$_2$—N, CH$_2$—CH$_2$, oxygen and sulfur;

wherein $R_1$ is selected from the group consisting of hydrogen, a lower alkyl group, a nitroso group, a formyl group and zero and $R_1$ is zero when B is oxygen or sulfur;

wherein $R_3$ is selected from the group consisting of hydrogen, a lower alkyl group and zero, and $R_3$ is zero when A is zero;

wherein $R_4$ is selected from the group consisting of hydrogen and a lower alkyl group;

wherein $R_5$ is selected from the group consisting of hydrogen and a lower alkyl group;

wherein $R_8$ is selected from the group consisting of naphthyl, mono-, di- and tri-substituted naphthyl, thionaphthyl, thiophenyl and hydroxyphenyl when $R_1$ is hydrogen and $R_4$ is hydrogen;

wherein $R_8$ is selected from the group consisting of phenyl, mono-, di- and tri-substituted phenyl, naphthyl, mono-, di- and tri-substituted naphthyl, pyridine and p-aroyl-L-glutamate when $R_1$ is a lower alkyl group and $R_4$ is hydrogen;

wherein $R_8$ is selected from the group consisting of pyridine, phenyl, mono-, di- and tri-substituted phenyl, naphthyl, and mono-, di- and tri-substituted naphthyl and p-aroyl-L-glutamate when $R_1$ is zero;

wherein $R_8$ is selected from the group consisting of phenyl, mono-, di- and tri-substituted phenyl, naphthyl, mono-, di- and tri-substituted naphthyl and p-aroyl-L-glutamate when $R_1$ is hydrogen and $R_4$ is a lower alkyl group; and wherein $R_8$ is not p-benzoyl-L-glutamate or pyridine when X is OH, A is zero, B is sulfur, $R_4$ is methyl and $R_5$ is hydrogen, and $R_8$ is not p-benzoyl-L-glutamate when X is OH, A is CH, B is CH, $R_4$ is hydrogen and $R_5$ is hydrogen; and wherein each lower alkyl group is independently selected from the group consisting of lower alkyl groups having from 1 to 6 carbons. referred embodiments of formula 1 are further recited in Table 1.

TABLE 1

| Compound | X | Y | L—M Bond | A | B | $R_1$ | $R_3$ | $R_4$ | $R_5$ | $R_8$ |
|---|---|---|---|---|---|---|---|---|---|---|
| 301 | NH$_2$ | NH$_2$ | dbl | CH | N | H | H | H | H | 1-naphthyl |
| 303 | NH$_2$ | NH$_2$ | dbl | CH | N | H | H | H | H | 4-OHphenyl |
| 304 | NH$_2$ | NH$_2$ | dbl | CH | N | CH$_3$ | H | H | H | 2,5-dimethoxy-phenyl |
| 305 | NH$_2$ | NH$_2$ | dbl | CH | N | CH$_3$ | H | H | H | 3,4-dichloro-phenyl |
| 306 | NH$_2$ | NH$_2$ | dbl | CH | N | CH$_3$ | H | H | H | 1-naphthyl |
| 307 | NH$_2$ | NH$_2$ | dbl | CH | S | —* | H | H | H | 3,4-dimethoxy-phenyl |
| 308 | NH$_2$ | NH$_2$ | dbl | CH | S | — | H | H | H | 3,4-dichloro-phenyl |
| 309 | NH$_2$ | NH$_2$ | dbl | CH | S | — | H | H | H | 1-naphthyl |
| 310 | NH$_2$ | NH$_2$ | dbl | CH | S | — | H | H | H | 2-naphthyl |
| 312 | NH$_2$ | NH$_2$ | dbl | CH | N | CH$_3$ | H | H | H | p-benzoyl-L-glutamate |
| 313 | OH | NH$_2$ | dbl | CH | N | H | H | CH$_3$ | H | p-benzoyl-L-glutamate |
| 314 | OH | NH$_2$ | dbl | CH | N—CH$_2$ | H | H | CH$_3$ | H | p-benzoyl-L-glutamate |
| 315 | OH | NH$_2$ | dbl | CH | S | — | H | CH$_3$ | H | 4-pyridine |
| 317 | OH | NH$_2$ | dbl | — | S | — | — | CH$_3$ | H | 3,4-dimethoxy-phenyl |
| 318 | OH | NH$_2$ | dbl | — | S | — | — | CH$_3$ | H | 3,4-dichloro-phenyl |
| 319 | OH | NH$_2$ | dbl | — | S | — | — | CH$_3$ | H | 4-chloro-phenyl |
| 320 | OH | NH$_2$ | dbl | — | S | — | — | CH$_3$ | H | 4-NO$_2$phenyl |
| 321 | OH | NH$_2$ | dbl | — | S | — | — | CH$_3$ | H | phenyl |
| 322 | OH | NH$_2$ | dbl | — | S | — | — | CH$_3$ | H | 2-naphthyl |

"—" indicates that the substituent is zero, that is, not present in the particular embodiment.

The most preferred embodiments of formula 1 are identified as compounds 312 and 320.

The present invention is further directed to methods of synthesizing 5-substituted pyrrolo [2,3-d] pyrimidines. Synthesis of these compounds according to the methods of the present invention can be accomplished by convergent synthesis. As will be understood by one skilled in the art, convergent synthesis involves the production of an intermediate product from which numerous additional compounds can be made. Here, the preferred intermediate product is 2,4-diamino-5-cyano pyrrolo-[2,3-d]pyrimidine.

More specifically, the present invention is directed to a method of synthesizing a compound, and pharmaceutically acceptable salts thereof, having the formula:

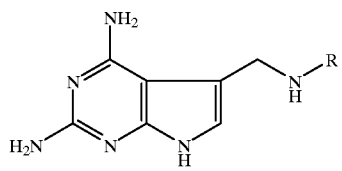

wherein R is selected from the group consisting of a lower alkyl group, a p-aroyl-L-glutamate group, an aryl group, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, alkyltriaryl group is the same or different and is selected from the group consisting of a lower alkyl group, an alkoxy, a substituted alkoxyaryloxy group and a halogen; and wherein each lower alkyl group is independently selected from the group consisting of lower alkyl groups having from about 1 to 6 carbons, comprising the steps of:
a) debrominating a pyrrole;
b) fusing the product of step a) with an amidine;
c) condensing the product of step b) with a nucleophile;
d) reducing the product of step c); and
e) purifying the compounds of step d).

Preferably, the debromination of step a) is performed in a mixture of dimethylformamide (DMF) and methanol under hydrogenation in the presence of a palladium catalyst. Either a 5% Pd—BaCO$_3$ or a 10% Pd—C catalyst can be used; 5% Pd—BaCO$_3$ is preferred. Typically, the debromination step will be completed in about 3 hours, and the reaction performed under hydrogen at a pressure of between about 40 and 60 psi, preferably at about 50 psi.

The fusion of step b) is preferably performed with chlorformamidine hydrochloride, and more preferably performed by heating a uniformly stirred suspension of the product of step a) and chlorformamidine hydrochloride in a liquid heat transfer media and heating to a temperature of between about 150° C. and 180° C., preferably between about 160° C. and 170° C., for a period of between about 36 and 50 hours, preferably about 48 hours. Any liquid heat transfer media can be used, including Dowtherm-A®, available from Dow Chemical Company.

The selective nucleophile as disclosed in condensing step c) is selected from the group consisting of an aniline, diethyl(p-aminoaroyl)-L-glutamate, N-methyl and diethyl (p-aminoaroyl)-L-glutamate. Any suitable aniline can be used, including but not limited to an aniline of the formula

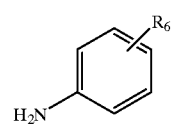

(3)

wherein R$_6$ is selected from the group consisting of 3',4',5'-trimethoxy, 3',4'-dimethoxy, 4'-methoxy, 2',5'-dimethoxy, 2',5'-diethoxy, 3',4'-dichloro, 2',3'-tetramethyl, hydrogen trimethoxy, dimethoxy and monomethoxy groups, trihalo, dihalo and monohalo groups, trialkyl, dialkyl and monoalkyl groups and combinations of methoxy groups, halo groups and lower alkyls.

These are the preferred anilines for use in the methods of the present invention.

Preferably, the condensation of step c) is performed in 70% to 80% acetic acid under hydrogenation, and in the presence of a Raney nickel catalyst. Hydrogenation times of from about 24 to 72 hours, and hydrogenation pressures of between about 50 and 60 psi, preferably 55 psi, are preferred. Under these conditions, the Schiff bases are expected to form.

Alternatively, condensation can be accomplished by heating a mixture of the product of step b) with formaldehyde and Raney nickel at a temperature between about 70° and 90° C., preferably 80° C., for about 2 hours.

Reduction of the Schiff bases, step d), is preferably performed by stirring a solution of the product of step c) in methanol at room temperature using NaCNBH as the reducing agent. In addition, 50% methanolic hydrochloric acid or glacial acetic acid can be used to maintain the pH of the reaction mixture at about 2. The reduction step should take about 4 hours.

Preferably, the purification of step e) is performed by a method selected from the group consisting of silica gel column chromatography and dissolution of the product of step d) in methanol, filtration, evaporation of the filtrate, and trituration of the residue in anhydrous diethylether.

When either diethyl(p-aminoaroyl)-L-glutamate or N-methyl diethyl(p-aminoaroyl)-L-glutamate are used in the condensation of step c), an additional hydrolysis step, step f), is preferably performed following step e). Preferably, the hydrolysis of step f) is accomplished by stirring a solution of the product of step e) in a 1:1 sodium hydroxide:methanol solution at room temperature for between about 60 and 84 hours, preferably about 72 hours.

Specific embodiments of these methods are discussed in the examples below.

Preferred embodiments of the compounds produced by the methods of the present invention are further recited in Table 2.

TABLE 2

| Compound Number | R Group |
|---|---|
| 1 | 3,4,5-trimethoxyphenyl |
| 2 | 3,4-dimethoxyphenyl |
| 3 | 2,5-dimethoxyphenyl |
| 4 | 4-methoxyphenyl |
| 5 | 2,5-diethoxyphenyl |
| 6 | 3,4-dichlorophenyl |

TABLE 2-continued

| Compound Number | R Group |
|---|---|
| 7 | 2',3'-(CH)$_4$phenyl |
| 8 | phenyl |
| 9 | p-benzoyl-L-glutamate |

Compounds 4, 8 and 9, as defined in the above table, are preferred for therapeutically treating cancer patients, and compounds 4 and 8 for therapeutically and prophylactically treating infections caused by *Pneumocystis carinii* and *Toxoplasmosis gondii*.

The present invention also provides pyrrolo-[2,3-d] pyrimidine compounds, and pharmaceutically acceptable salts thereof, having the formula (9):

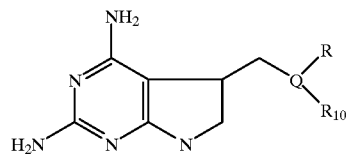

wherein Q is selected from the group consisting of nitrogen and sulfur;

wherein R is selected from the group consisting of a lower alkyl group, a p-aroyl-L-glutamate group, an aryl group, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, alkyltriaryl group is the same or different and is selected from the group consisting of a lower alkyl group, an alkoxy, a substituted alkoxyaryloxy group and a halogen;

wherein $R_{10}$ is selected from the group consisting of hydrogen and a lower alkyl group; and wherein $R_{10}$ is a lower alkyl when Q is nitrogen.

Methods of synthesizing compounds having formula 9 as described above are also provided. These methods comprise the steps of:

a) debrominating a pyrrole;
b) fusing the product of step a) with an amide;
c) condensing the product of step b) with a nucleophile;
d) reducing the product of step c); and
e) purifying the compounds of step d); wherein the nucleophile of step c) is a compound having the general structure

wherein Q is selected from the group consisting of nitrogen and sulfur;

wherein R is selected from the group consisting of a lower alkyl group, a p-aroyl-L-glutamate group, an aryl group, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, alkyltriaryl group is the same or different and is selected from the group consisting of a lower alkyl group, an alkoxy, a substituted alkoxyaryloxy group and a halogen;

wherein $R_{10}$ is selected from the group consisting of hydrogen and a lower alkyl group; and wherein $R_{10}$ is a lower alkyl when Q is nitrogen.

The present invention is also directed to furo[2,3-d] pyrimidine compounds, and pharmaceutically acceptable salts thereof, having the following general formula:

(4)

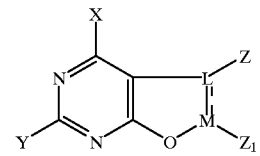

wherein X and Y are the same or different and are selected from the group consisting of OH and $NH_2$;

wherein L and M are selected from the group consisting of carbon and CH, the chemical bond between L and M is selected from the group consisting of a single bond and a double bond, L and M are carbon when the bond is a double bond, and L and M are CH when the bond is a single bond;

wherein Z and $Z_1$ are different and are selected from the group consisting of $R_4$ and

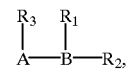

where Z is $R_4$ when $Z_1$ is

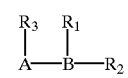

and Z is

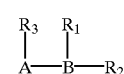

when $Z_1$ is $R_4$;

wherein A is selected from the group consisting of CH and zero;

wherein B is selected from the group consisting of sulfur, nitrogen, oxygen, CH, N—CH$_2$, CH$_2$—N, CH$_2$—CH$_2$, and zero;

wherein $R_1$ is selected from the group consisting of hydrogen, a lower alkyl group, a nitroso group, a formyl group and zero and $R_1$ is zero when B is sulfur, oxygen or zero;

wherein $R_2$ is selected from the group consisting of a lower alkyl group, p-aroyl-L-glutamate, an aryl group, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, alkyltriaryl group is the same or different and is selected from the group consisting of a lower alkyl, an alkoxy, an alkoxyaryloxy group, a halogen and zero but $R_2$ is not 3,4,5-trimethoxyphenyl, 3,4,5-trichlorophenyl, 3,4-dichlorophenyl, 2,5-dimethoxyphenyl or a p-benzoyl-L-glutamate when $R_1$ is hydrogen and $R_4$ is hydrogen, and $R_2$ is not p-benzoyl-L-glutamate when $R_1$ is methyl;

wherein $R_3$ is selected from the group consisting of hydrogen, a lower alkyl group, and zero and $R_3$ is zero when A is zero;

wherein $R_4$ is selected from the group consisting of hydrogen, a lower alkyl group and S—$R_7$ where $R_7$ is selected from the group consisting of phenyl, mono-, di- and tri-substituted phenyl, naphthyl, mono-, di- and tri-substituted naphthyl and p-aroyl-L-glutamate; and wherein each lower alkyl group is independently selected from the group consisting of lower alkyl groups having from 1 to 6 carbons.

Particularly preferred embodiments of formula 4 are recited below in Table 3. For all of the embodiments described in Table 3, X is $NH_2$, Y is $NH_2$ and the bond between L and M is a double bond.

TABLE 3

| Compound | A | B | $R_1$ | $R_2$ | $R_3$ | $R_4$ |
|---|---|---|---|---|---|---|
| 159 | CH | S | — | phenyl | H | H |
| 160 | CH | S | — | 1-naphthyl | H | H |
| 161 | CH | S | — | 2-naphthyl | H | H |
| 162 | CH | N | H | 1-naphthyl | H | H |
| 163 | CH | N | H | 2-naphthyl | H | H |
| 164 | CH | O | — | 2-naphthyl | H | H |
| 165 | CH | N | H | 2-phenoxyphenyl | H | H |
| 166 | CH | N | H | 4-phenoxyphenyl | H | H |
| 167 | CH | N | H | 2-phenylphenyl | H | H |
| 169 | CH | N | H | 2',5'-dichlorophenyl | H | H |
| 171 | CH | N | $CH_3$ | 3',4'-dichlorophenyl | H | H |
| 172 | CH | N | $CH_3$ | 3',4',5'-trichlorophenyl | H | H |
| 175 | CH | N | H | 3'-methoxyphenyl | H | H |
| 177 | CH | H | — | — | H | S—$R_7$* |
| 178 | CH | H | — | — | H | S—$R_7$† |
| 179 | — | — | — | phenyl | — | H |

*$R_7$ equals 1-naphthyl
†$R_7$ equals 2-naphthyl

Compounds 161 and 167 as described in Table 3 are most preferred for therapeutically treating cancer patients, and therapeutically and prophylactically treating infections caused by *Pneumocystis carinii* and *Toxoplasmosis gondii*.

The present invention is also directed to methods for synthesizing the compound, and pharmaceutically acceptable salts thereof, having the formula (4)

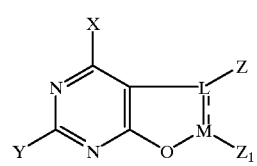

wherein X and Y are the same or different and are selected from the group consisting of OH and $NH_2$;

wherein L and M are selected from the group consisting of carbon and CH, the chemical bond between L and M is selected from the group consisting of a single bond and a double bond, L and M are carbon when the bond is a double bond, and L and M are CH when the bond is a single bond;

wherein Z and $Z_1$ are different and are selected from the group consisting of $R_4$ and

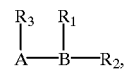

where Z is $R_4$ when $Z_1$ is

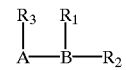

and Z is

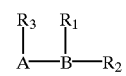

when $Z_1$ is $R_4$;

wherein A is selected from the group consisting of CH and zero;

wherein B is selected from the group consisting of sulfur, nitrogen, oxygen, CH, N—$CH_2$, $CH_2$—N, $CH_2$—$CH_2$, and zero;

wherein $R_1$ is selected from the group consisting of hydrogen, a lower alkyl group, a nitroso group, a formyl group and zero and $R_1$ is zero when B is sulfur, oxygen or zero;

wherein $R_2$ is selected from the group consisting of a lower alkyl group, p-aroyl-L-glutamate, an aryl group, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, alkyltriaryl group is the same or different and is selected from the group consisting of a lower alkyl group, an alkoxy, an alkoxyaryloxy group, a halogen and zero, but $R_2$ is not 3,4,5-trimethoxyphenyl, 3,4,5-trichlorophenyl, 3,4-dichlorophenyl, 2,5-dimethoxyphenyl or p-benzoyl-L-glutamate when $R_1$ is hydrogen and $R_4$ is hydrogen, and $R_2$ is not p-benzoyl-L-glutamate when $R_1$ is methyl;

wherein $R_3$ is selected from the group consisting of hydrogen, a lower alkyl group, and zero and $R_3$ is zero when A is zero;

wherein $R_4$ is selected from the group consisting of hydrogen, a lower alkyl group and S—$R_7$ where $R_7$ is selected from the group consisting of phenyl, mono-, di- and tri-substituted phenyl, naphthyl, mono-, di- and tri-substituted naphthyl and p-aroyl-L-glutamate,; and wherein each lower alkyl group is independently selected from the group consisting of lower alkyl groups having from 1 to 6 carbons, comprising the steps of:

a) stirring a pyrimidine and a substituted acetone in a solvent;

b) purifying the product of step a);
c) performing nucleophilic displacement of the chloride in the product of step b); and
d) purifying the product of step c).

In one embodiment of the methods described above, step a) is performed by stirring one equivalent each of 2,6-diamino-4-hydroxypyrimidine and 1,3-dichloroacetone in DMF at room temperature for a period of between about 12 and 36 hours, preferably 24 hours.

Purification of the product of step a) can be accomplished by any means known in the art; column chromatography is preferred. The product resulting from the purification step b) is not generally stable for long durations at room temperature. It is, therefore, preferred that the nucleophilic displacement of step c) be performed within about 1 hour of completion of step b).

The nucleophilic displacement of step c) can be accomplished by any of various compounds including those selected from the group consisting of (p-aminoaroyl)-L-glutamic acid, diethyl N-(p-methylaminoaroyl)glutamate, and a nucleophile. As used in reference to the methods for synthesizing a compound, and pharmaceutically acceptable salts thereof, having formula (4), nucleophile includes, but is not limited to aniline, substituted analines, phenols, thiophenols and substituted phenols and thiophenols.

When step c) is performed with (p-aminoaroyl)-L-glutamic acid, the purification of step d) is preferably performed by precipitating the product of step c) by diluting said product with a suitable solvent, preferably water, and separating said product from unreacted starting materials and impurities by any means known in the art; cellulose column chromatography is preferred. Acidification of the product is then preferred.

When the nucleophilic displacement of step c) is performed with diethyl N-[p-methylamino(aroyl)]glutamate, the purification of step d) is preferably accomplished by stirring the product of step c) with 1N sodium hydroxide at room temperature for between about 12 to 36, preferably 24 hours, followed by acidification.

Alternatively, when conducting the nucleophilic displacement with (p-aminoaroyl)-L-glutamic acid, the desired product can also be obtained by reductive methylation of the intermediate with a suitable aldehyde, preferably formaldehyde, and sodium cyanoborohydride at a pH of approximately 6 to 7. Purification is then accomplished by any means known in the art, preferably by wet cellulose column, and acidification of the product performed.

When the nucleophilic displacement reactions are accomplished with an aniline, the product of step b) is preferably mixed with anhydrous dimethylsulfoxide and two equivalents of potassium carbonate for approximately 60 to 84 hours, preferably 72 hours, at room temperature. Heating the reaction mixture to between about 35° and 45° C. for a period of between about 60 and 84 hours, preferably 72 hours, increases the yield of the desired product. The product is then isolated from impurities and other unreacted starting materials by any means known in the art. Preferably, isolation is accomplished by adding excess water to the reaction mixture and stirring at room temperature for a period of approximately 6 to 8 hours to separate the product; chromatographic purification is then performed.

The present invention is also directed to compounds, and pharmaceutically acceptable salts thereof, having the general formula 5

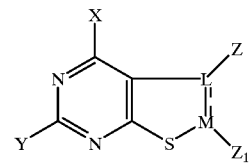

(5)

wherein X and Y are the same or different and are selected from the group consisting of OH and $NH_2$;

wherein L and M are selected from the group consisting of carbon and CH, the chemical bond between L and M is selected from the group consisting of a single bond and a double bond, L and M are carbon when the bond is a double bond, and L and M are CH when the bond is a single bond;

wherein Z and $Z_1$ are different and are selected from the group consisting of $R_4$ and

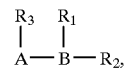

where Z is $R_4$ when $Z_1$ is

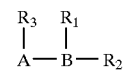

and Z is

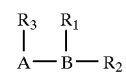

when $Z_1$ is $R_4$;

wherein A is selected from the group consisting of CH and zero;

wherein B is selected from the group consisting of sulfur, nitrogen, oxygen, CH, N—$CH_2$, $CH_2$—N, $CH_2$—$CH_2$, and zero;

wherein $R_1$ is selected from the group consisting of hydrogen, a lower alkyl group, a nitroso group, a formyl group and zero and $R_1$ is zero when B is sulfur, oxygen or zero;

wherein $R_2$ is selected from the group consisting of a lower alkyl group, an aryl group, p-aroyl-L-glutamate, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, alkyltriaryl group is the same or different and is selected from the group consisting of a lower alkyl group, an alkoxy, an alkoxyaryloxy group, a halogen and zero;

wherein $R_3$ is selected from the group consisting of hydrogen, a lower alkyl group and zero, and $R_3$ is zero when A is zero;

wherein $R_4$ is selected from the group consisting of hydrogen and lower alkyl group; and wherein each lower alkyl group is independently selected from the group consisting of lower alkyl groups having from about 1 to 6 carbons.

The present invention is also directed to compounds, and pharmaceutically acceptable salts thereof, having the general formula:

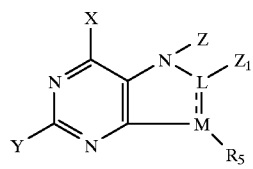

(6)

wherein X and Y are the same or different and are selected from the group consisting of OH and $NH_2$;

wherein L and M are selected from the group consisting of carbon and CH, the chemical bond between L and M is selected from the group consisting of a single bond and a double bond, L and M are carbon when the bond is a double bond, and L and M are CH when the bond is a single bond;

wherein Z and $Z_1$ are different and are selected from the group consisting of $R_4$ and

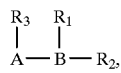

where Z is $R_4$ when $Z_1$ is

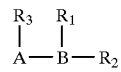

and Z is

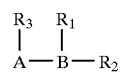

when $Z_1$ is $R_4$;

wherein A is selected from the group consisting of CH and zero;

wherein B is selected from the group consisting of sulfur, nitrogen, oxygen, CH, N—$CH_2$, $CH_2$—N, $CH_2$—$CH_2$, and zero;

wherein $R_1$ is selected from the group consisting of hydrogen, a lower alkyl group, a nitroso group, a formyl group and zero, and $R_1$ is zero when B is sulfur, oxygen or zero;

wherein $R_2$ is selected from the group consisting of a lower alkyl group, p-aroyl-L-glutamate, an aryl group, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, or alkyltriaryl group is the same or different and is selected from the group consisting of a lower alkyl group, an alkoxy, an alkoxyaryloxy group, a halogen and zero;

wherein $R_3$ is selected from the group consisting of hydrogen, a lower alkyl group and zero, and $R_3$ is zero when A is zero;

wherein $R_4$ is selected from the group consisting of hydrogen and lower alkyl group;

wherein $R_5$ is selected from the group consisting of hydrogen and lower alkyl group; and wherein each lower alkyl group is independently selected from the group consisting of lower alkyl groups having from about 1 to 6 carbons.

In preferred embodiments of formula 6, Y and X are $NH_2$, the bond between L and M is a double bond, A is zero, B is CH, $R_1$ is hydrogen, $R_2$ is selected from the group consisting of phenyl and 3,4-dichlorophenyl, $R_3$ is zero, $R_4$ is selected from the group consisting of hydrogen and lower alkyl and $R_5$ is selected from the group consisting of hydrogen and lower alkyl.

The present invention is also directed to compounds, and pharmaceutically acceptable salts thereof, having the general formula:

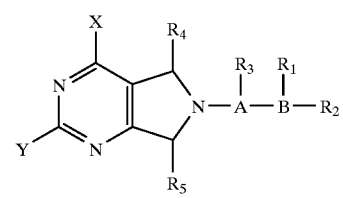

(7)

wherein X and Y are the same or different and are selected from the group consisting of OH and $NH_2$;

wherein A is selected from the group consisting of CH and zero;

wherein B is selected from the group consisting of sulfur, nitrogen, oxygen, CH, N—$CH_2$, $CH_2$—N, $CH_2$—$CH_2$, and zero;

wherein $R_1$ is selected from the group consisting of hydrogen, a lower alkyl group, a nitroso group, a formyl group and zero and $R_1$ is zero when B is sulfur, oxygen or zero;

wherein $R_2$ is selected from the group consisting of a lower alkyl group, p-aroyl-L-glutamate, an aryl group, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, or alkyltriaryl group is the same or different and is selected from the group consisting of a lower alkyl group, an alkoxy, an alkoxyaryloxy group, a halogen and zero;

wherein $R_3$ is selected from the group consisting of hydrogen, a lower alkyl group, and zero, and $R_3$ is zero when A is zero;

wherein $R_4$ is selected from the group consisting of hydrogen and lower alkyl group; and wherein each lower alkyl group is independently selected from the group consisting of lower alkyl groups having from about 1 to 6 carbons.

Figure 5:
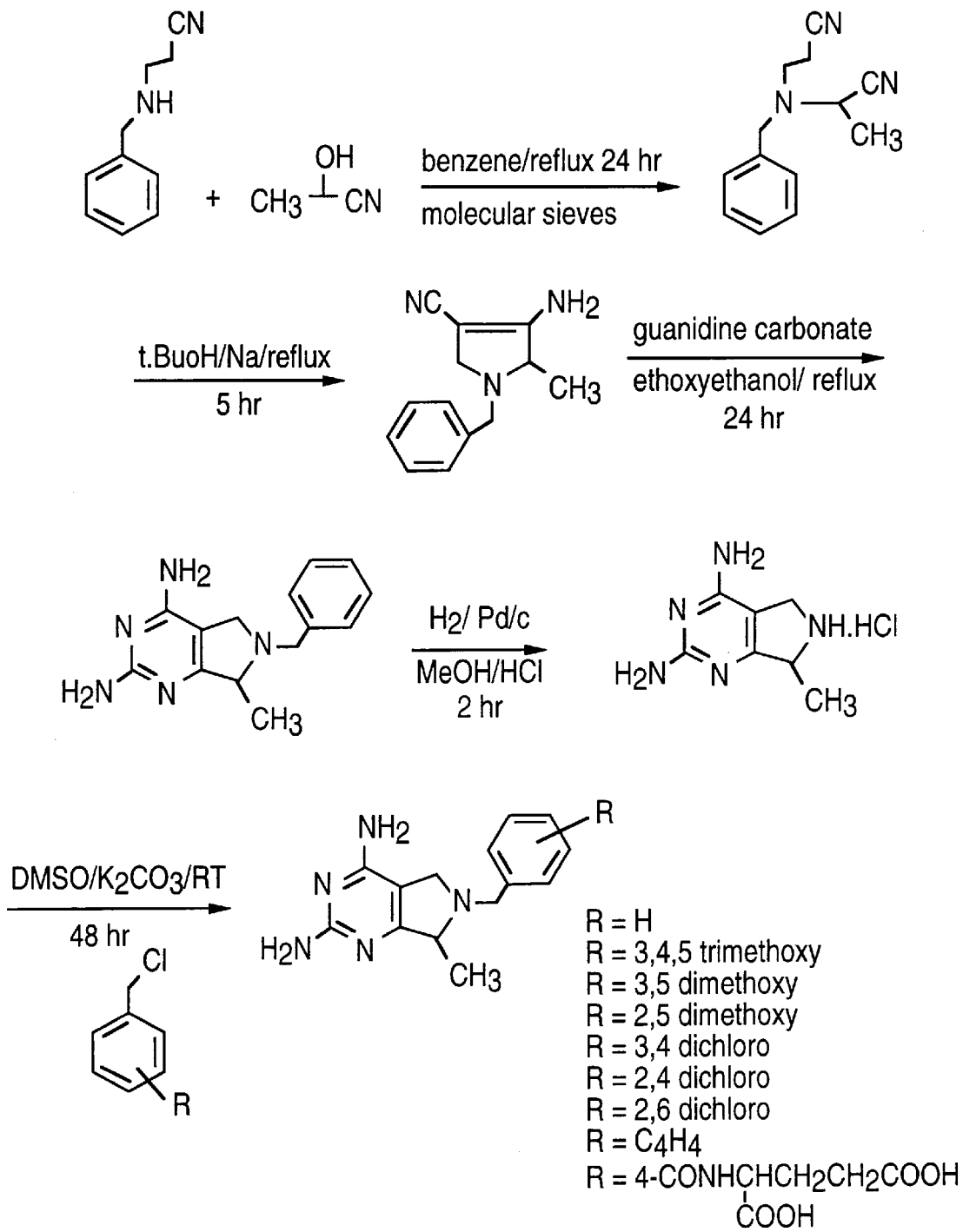
FIG. 5 shows a schematic diagram of the methods of preparing several compounds having formula 7.

In preferred embodiments of formula 7, X and Y are $NH_2$, A is zero, B is CH, $R_1$ is hydrogen, $R_2$ is selected from the group consisting of 3,4,5-trimethoxybenzyl, 3,5-dimethoxybenzyl, 2,5-dimethoxybenzyl, 3,4-dichlorobenzyl, 2,6-dichlorobenzyl, 2,4-dichlorobenzyl, 2-$CH_2$-naphthyl, $C_4H_4$benzyl and 4-benzyl-L-glutamate, $R_3$ is zero, $R_4$ is hydrogen, and $R_5$ is selected from the group consisting of hydrogen and methyl. The most preferred embodiments of formula (7) are illustrated in FIG. 5.

The present invention is also directed to compounds, and pharmaceutically acceptable salts thereof, having the formula:

(8)

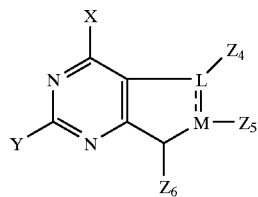

wherein X and Y are the same or different and are selected from the group consisting of OH and $NH_2$;

wherein L and M are selected from the group consisting of carbon and CH, the chemical bond between L and M is selected from the group consisting of a single bond and a double bond, L and M are carbon when the bond is a double bond, and L and M are CH when the bond is a single bond;

wherein $Z_4$, $Z_5$ and $Z_6$ are different and are selected from the group consisting of $R_4$, $R_5$ and

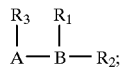

wherein A is selected from the group consisting of CH, sulfur and zero;

wherein B is selected from the group consisting of sulfur, nitrogen, oxygen, CH, N—$CH_2$, $CH_2$—N, $CH_2$—$CH_2$, and zero;

wherein $R_1$ is selected from the group consisting of hydrogen, a lower alkyl group, a nitroso group, a formyl group and zero, and $R_1$ is zero when B is sulfur, oxygen or zero;

wherein $R_2$ is selected from the group consisting of a lower alkyl group, p-aroyl-L-glutamate, an aryl group, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, or alkyltriaryl group is the same or different and is selected from the group consisting of a lower alkyl group, an alkyl group, an alkoxy, an alkoxyaryloxy group, a halogen and zero;

wherein $R_3$ is selected from the group consisting of hydrogen, a lower alkyl group and zero, and $R_3$ is zero when A is zero;

wherein $R_4$ is selected from the group consisting of hydrogen and a lower alkyl group;

wherein $R_5$ is selected from the group consisting of hydrogen and a lower alkyl group;

where $R_4$ is the same or different than $R_5$;

wherein each of said $R_4$, $R_5$ and

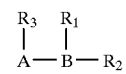

substituents is used once; and X wherein each lower alkyl group is independently selected from the group consisting of lower alkyl groups having from about 1 to 6 carbons.

In a preferred embodiment of formula 8, X and Y are $NH_2$, the bond between L and M is single, A is sulfur, B is carbon, $R_1$ is hydrogen, $R_2$ is phenyl and $R_3$ is zero.

For all of the formulas described above, the lower alkyl groups are the same or different and are independently selected from those lower alkyl groups having one to six carbon atoms, such as for example methyl, ethyl, propyl, butyl, pentyl, hexyl, cyclopropyl, cyclobutyl, cyclohexyl, cyclopropylmethyl or cyclobutylmethyl groups. Alkyl groups sharing one to about six carbon atoms are preferred. These lower alkyl groups are straight chain, branched chain or cyclic (alicyclic hydrocarbon) arrangements. The carbon atoms of these straight chain, branched chain or cyclic arranged alkyl groups may have one or more substituents for the hydrogens attached to the carbon atoms.

Suitable aryl groups include for example phenyl and benzyl groups. Suitable substituted aryl groups include for example: mono-, di- and tri-substituted alkoxy phenyl groups; mono-, di- and tri-halogenated phenyl groups; mono-, di and tri-substituted alkyl phenyl groups; mono-, di- and tri-substituted alkoxy benzyl groups and mono-, di- and tri-substituted halogenated benzyl groups.

The term "alkylaryl" refers to groups having an alkyl moiety attached to an aryl ring such as a phenyl or benzyl ring. The alkyl moiety is preferably a lower alkyl chain having one to about seven carbon atoms. This alkyl moiety may also contain oxygen, nitrogen or sulfur atoms, such as for example methoxy groups. The aryl moiety of the alkylaryl group is unsubstituted, mono-substituted, di-substituted or tri-substituted. If substituted, each substituent may independently be selected from the group consisting of a lower alkyl group having one to about seven carbon atoms, an alkoxy group such as for example a methoxy group and a halogen, such as for example fluorine, chlorine or bromine.

Other substituent groups in the formulas 1–8 as described above are as follows: the alkylaryl group is selected from the group consisting of an alkylphenyl and alkylbenzyl group; the alkyldiaryl group is selected from the group consisting of alkylnaphthyl, alkylbenzothiophene, alkylindene, alkylbenzofuran, alkylindole and alkylaminoquinoline; the alkyltriaryl group is an alkylanthracyl group; the substituted aryl, diaryl and triaryl group is selected from the group consisting of a mono-, di- and tri-substituted alkylphenyl and alkylbenzyl group, alkylnaphthyl, alkylbenzothiophene, alkylindole, alkylbenzofuran, alkylindene, alkylaminoquinoline, alkylanthracyl; each substituted alkyldiaryl and alkyltriaryl group is selected from the group consisting of a mono-, di- and tri-substituted alkylnaphthyl, alkylbenzothiophene, alkylindole, alkylbenzofuran, alkylindene, alkylaminoquinoline and alkylanthracyl group; and each substituent is the same or different and is selected from the group consisting of methyl, ethyl, n-propyl, n-butyl, branched n-pentyl, branched pentyl, n-hexyl, branched hexyl, cyclopropyl, cyclobutyl, cyclopentyl, cyclohexyl, methoxy group, chlorine atom, bromine atom and fluorine atom.

In some embodiments of this invention, the compounds, and pharmaceutically acceptable salts thereof, having the general formula 1, 2 and 4–8 wherein X and Y are each $NH_2$, $R_1$ is selected from the group consisting of H, $CH_3$ and CHO, $CH_3$CHO, and zero and R and $R_2$ are selected from the group consisting of 2,5-dimethoxyphenyl, 2,3,4-trimethoxyphenyl, 2,4,6-trimethoxyphenyl, naphthyl, 4-methoxynaphthyl, anthracyl and methoxy anthracyl, florene, benzothiophene, indene, benzofuran, indole, aminoquinoline, 2,3-dichlorophenyl, 2,4-dichlorophenyl, 2,5-dichlorophenyl, 2,6-dichlorophenyl, 3,4-dichlorophenyl and 3,5-dichlorophenyl. $R_3$ is $CH_3$ or hydrogen, $R_4$ is either hydrogen, methyl, ethyl, propyl and butyl group, cyclopropyl, cyclobutyl and cyclohexyl or zero, B is selected from the group consisting of nitrogen, carbon, sulfur and oxygen, A is selected from the group consisting of nitrogen, carbon and sulfur.

In other embodiments of this invention, compounds and pharmaceutically acceptable salts thereof, are provided having the formulas 1, 2 and 4–8 wherein X and Y are each $NH_2$. $R_1$ is selected from the group consisting of H, $CH_3$, NO and CHO, $CH_3$CHO, zero. R and $R_2$ are selected from the group consisting of 2-methoxyphenyl, 3-methoxyphenyl, 4-methoxyphenyl, 2,4-dimethoxyphenyl, 3,4-dimethoxyphenyl, 3,5-dimethoxyphenyl, 2-chlorophenyl, 3-chlorophenyl, 4-chlorophenyl, 2,3,4-trichlorophenyl, 2,4,5-trichlorophenyl, 2,4,6-trichlorophenyl, 3,4,5-trichlorophenyl, 2-bromophenyl, 3-bromophenyl, 4-bromophenyl, 2,4-dibromophenyl, 2,5-dibromophenyl, 2,6-dibromophenyl, 3,4-dibromophenyl, 3,5-dibromophenyl, 2,4,6-tribromophenyl, 2-fluorophenyl, 3-fluorophenyl, 4-fluorophenyl, 2,3-difluorophenyl, 2,4-difluorophenyl, 2,5-difluorophenyl, 2,6-difluorophenyl, 3,4-difluorophenyl, 3,5-difluorophenyl, 2,3,4-trifluorophenyl, 2,4,5-trifluorophenyl, 2,4,6-trifluorophenyl, 2-methylphenyl, 3-methylphenyl, 4-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4,5-trimethylphenyl, and 2,4,6-trimethylphenyl. $R_3$ is $CH_3$ or hydrogen, and in formulas 3–5. $R_4$ is selected from the group consisting of hydrogen, methyl, ethyl, propyl, and butyl group, cyclopropyl, cyclobutyl, cyclohexyl and zero. B is selected from the group consisting of nitrogen, carbon, sulfur and oxygen and A is selected from the group consisting of nitrogen, carbon and sulfur.

In other embodiments of this invention, compounds and pharmaceutically acceptable salts thereof, are provided having the formulas 1, 2 and 4–8 wherein X and Y are each $NH_2$. $R_1$ is selected from the group consisting of H, $CH_3$, NO and CHO, $CH_3$CHO, zero. R and $R_2$ are selected from the group consisting of methyl, ethyl, n-propyl, n-butyl, cyclopropyl, cyclobutyl, cyclopentyl, cyclohexyl, 2-methoxybenzyl, 3,4-dimethoxybenzyl, 2,3-dimethoxybenzyl, 3,4-dimethoxybenzyl, 2,3,4-trimethoxybenzyl, 3,4,5-trimethoxybenzyl, 2-chlorobenzyl, 3,4-dichlorobenzyl, 2,3-dichlorobenzyl, 2,4-dichlorobenzyl, 2,5-dichlorobenzyl, 2,6-dichlorobenzyl, 2,6-dichlorobenzyl, 3,4-dichlorobenzyl, 3,5-dichlorobenzyl, 2-bromobenzyl, 3,4-dibromobenzyl, 2-fluorobenzyl, 3,4-difluorobenzyl, 2,4-difluorobenzyl, 2,5-difluorobenzyl, 2,6-difluorobenzyl and 3,4-difluorobenzyl. $R_3$ is $CH_3$ and hydrogen, and in formulas 3–5 $R_4$ is selected from the group consisting of a hydrogen, methyl, ethyl, propyl, butyl group, cyclopropyl, cyclobutyl, cyclohexyl; B is selected from the group consisting of nitrogen, carbon, sulfur and oxygen; and A is selected from the group consisting of nitrogen, carbon and sulfur.

The present invention further relates to methods of using the above-described compounds, and pharmaceutically acceptable salts thereof, in therapeutically an/or prophylactically treating a patient with an illness. As used herein, the term "illness" refers to cancer, infection by *Pneumocystis carinii*, infection by *Toxoplasmosis gondii*, or other secondary infections arising in immunocompromised patients, such as those with AIDS, and infections caused by bacteria, malaria, fungi or protozoa.

A method of therapeutically treating a patient for an illness comprises the steps of:

a) employing a compound, or pharmaceutically acceptable salts thereof, having any of the above formulas 1, 2 or 4–9;

b) incorporating said compound in a suitable pharmaceutical carrier; and c) administering a therapeutically effective amount of said compound incorporated in said carrier to a patient.

As used herein, the term "suitable pharmaceutical carrier" refers to any pharmaceutical carrier known in the art, absent compatibility problems with the compounds of formula 1, 2 or 4–9. Preferred carriers include physiologic saline and 5% dextrose.

As used herein, the term "therapeutically effective amount" refers to that amount of any of said compounds of formulas 1, 2 or 4–9 incorporated in a suitable pharmaceutical carrier which is required to bring about a desired effect, such as reducing tumor size, destroying cancerous cells or resisting/treating infection caused by organisms such as *Pneumocystis carinii* and *Toxoplasmosis gondii*.

As will be understood by one skilled in the art, a therapeutically effective amount of said compound can be administered by any means known in the art, including but not limited to, injection, parenterally, orally, or, where appropriate, topically.

It is well within the skill of one practicing in the art to determine what dosage, and the frequency of this dosage, which will constitute a therapeutically effective amount for each individual patient, depending on the type of illness and the severity of such illness. It is also within the skill of one practicing in the art to select the most appropriate method of administering the compounds based upon the needs of each patient.

Methods of prophylactically treating a patient for an illness comprise the steps of:

a) employing a compound, or pharmaceutically acceptable salts thereof, having any of the formulas 1, 2 or 4–9 as described above;

b) incorporating said compound in a suitable pharmaceutical carrier; and c) administering a prophylactically effective amount of said compound incorporated in said carrier to a patient; wherein said illness is selected from the group consisting of infection caused by *Pneumocystis carinii* and *Toxoplasmosis gondii*.

As used herein, the term "prophylactically effective amount" refers to that amount of any of the compounds described above which will cause the body to generate antibodies in amounts sufficient to resist the onset of infection caused by *Pneumocystis carinii* or *Toxoplasmosis gondii* in immunocompromised patients.

As will be understood by one skilled in the art, a prophylactically effective amount of said compound can be administered by any means known in the art, including but not limited to, injection, parenterally, orally, or, where appropriate, topically.

It is well within the skill of one practicing in the art, to determine what dosage, and the frequency of this dosage, which will constitute a prophylactically effective amount for each individual patient, depending on the type of illness, such as the type of cancer, and the severity of such illness. It is also within the skill of one practicing in the art to select the most appropriate method of administering the compounds based upon the needs of each patient.

EXAMPLES

The following examples are set forth to illustrate various embodiments of the invention, and should not be construed as limiting the invention in any way. Standard test procedures familiar to those skilled in the art were used in the examples, such as those procedures described by Gangjee, A., et al., in "5-Arylthio-substituted 2-amino-4-oxo-6-methyl pyrrolo]2,3-d]pyrimidine antifolates as thymidylate synthase inhibitors and antitumor agents", *J. Med. Chem.*, Vol. 38, pp. 4495–4502 (1995); "Effect of bridge region variation on antifolate and antitumor activity of classical 5-substituted 2,4-diamino furo [2,3-d] pyrimidines", *J. Med. Chem.*, Vol. 38, pp. 3798–3805 (1995); and "Novel 2,4-diamino-5-substituted-pyrrolo[2,3-d]pyrimidines As Classical and Non-Classical Antifolate Inhibitors of Dihydrofolate Reductases", *J. Med. Chem.*, Vol. 38, pp. 2158–2165 (Jun. 6, 1995) and references disclosed therein.

Example I

Compounds 1–6, 8, 301 and 303–312 were evaluated as inhibitors of dihydrofolate reductase (DHFR) from *Pneumocystis carinii* (Pc), *Toxoplasmosis gondii* (Tg) and rat liver (RL). Performance of these compounds was compared with that of trimetrexate (TMQ), piritrexim (PTX), trimethoprim (TMP) and methotroxate (MTX), all of which are currently available. Trimetrexate is available from Warner-Lambert/Parke Davis Pharmaceutical Research, Ann Arbor, Mich. Trimetrexate is approved by the United States Food and Drug Administration as an approved new drug for the treatment of *Pneumocystis carinii* infections in patients with AIDS. PTX is an experimental anticancer agent in Phase II clinical trials and is also an agent against *Pneumocystis carinii* and *Toxoplasmosis gondii*. TMP is an agent used against *Pneumocystis carinii* infection in conjunction with sulfonamides. MTX is a clinical used anticancer agent.

The evaluations of Compounds 1–6, 8, 301 and 303–312 consisted of determining the $IC_{50}$ values and selectivity ratios of each compound against *Pc* DHFR, *Tg* DHFR and RL DHFR. The $IC_{50}$ value is the concentration of a compound required to inhibit the dihydrofolate reductase activity by 50 percent (%). It will be understood by those skilled in the art that the lower the $IC_{50}$ value the more potent the compound. The selectivity ratio is a measure of the selectivity of a compound for *Pc* DHFR or *Tg* DHFR and is expressed as the $IC_{50}$ value of the DHFR from rate liver (RL) divided by the $IC_{50}$ value of either the *Pc* DHFR or the *Tg* DHFR, depending on which organism the compounds are being tested against. For example, the selectivity ratio of a compound is calculated by the following formula:

$$\frac{IC_{50}\,RL\,DHFR}{IC_{50}(Pc\,DHFR \text{ or } Tg\,DHFR)}$$

It will be understood by those skilled in the art that the higher the selectivity ratio, the less toxic the compound is to mammalian dihydrofolate reductase, and thus, less toxic to the patient.

Table 4 sets forth the $IC_{50}$ values for *Pc* DHFR, RL DHFR and *Tg* DHFR and the corresponding selectivity ratios for the compounds tested.

TABLE 4

Inhibitory Concentrations ($IC_{50}\,\mu M$) and Selectivity Ratios

| Compound # | Pc DHFR[1] | RL DHFR[1] | Selectivity Ratio: RL DHFR/Pc DHFR | Tg DHFR[1] | Selectivity Ratio: RL DHFR/Tg |
|---|---|---|---|---|---|
| 1 | >23 | 56.3 | <2.4 | 8.1 | 7.0 |
| 2 | 119.0 | 116.0 | 1.0 | 4.3 | 27.0 |
| 3 | 279.0 | 63.0 | 0.23 | 6.0 | 10.5 |
| 4 | 45.7 | 156.0 | 3.4 | 1.7 | 92.0 |
| 5 | >21 | 70.0 | <3.3 | 5.3 | 13.2 |
| 6 | 35.3 | 14.4 | 0.4 | 1.4 | 10.3 |
| 8 | 252.0 | >252 | >1 | 3.9 | >65 |
| 9 | 0.038 | 0.044 | 1.20 | 0.21 | 0.21 |
| 301 | 307.0 | 59.3 | 0.2 | 1.1 | 53.9 |
| 303 | 81.0 | 4.2 | 0.05 | 1.4 | 3.0 |
| 304 | >12.0 | >12.0 | ND* | 3.4 | >4.0 |
| 305 | 28.90 | 3.0 | 0.11 | 1.0 | 3.0 |
| 306 | 209.0 | 8.20 | 0.04 | 0.87 | 9.43 |
| 307 | 11.10 | 16.7 | 1.50 | 2.60 | 6.42 |
| 308 | 58.50 | 5.30 | 0.09 | 11.6 | 0.46 |
| 309 | 10.60 | 3.00 | 0.28 | 0.81 | 3.70 |
| 310 | 929.0 | 82.9 | 0.09 | 9.20 | 9.01 |
| 312 | 0.044 | 0.06 | 1.36 | 0.15 | 0.40 |
| TMQ | 0.042 | 0.003 | 0.07 | 0.01 | 0.30 |
| PTX | 0.038 | 0.001 | 0.04 | 0.01 | 0.14 |
| TMP | 12.0 | 133.0 | 11.1 | 2.7 | 49.0 |
| MTX | 0.001 | 0.003 | 3.0 | 0.014 | 0.21 |

*ND = not determined

As can be seen from the above table, Compound 4 is almost two-times as selective at TMP and 306 times as selective as TMQ. Compound 8 similarly showed much higher selectivity than the compounds known in the art. These two compounds, therefore, represent preferred embodiments of the invention for the treatment of infections caused by *Pneumocystis carinii* and *Toxoplasmosis gondii* as well as in treatment of cancer patients as an antitumor agent or to destroy cancerous cells. With regard to *Pneumocystis carinii*, Compounds 4 and 8, with their high potency and high selectivity, may be used clinically with a lesser amount of a leucovorin as compared to TMQ or may be used clinically without the necessity of leucovorin, and thus greatly reduce the cost of administering these compounds to a patient.

Example 2

Compound 9 was tested for DHFR inhibition against the growth of human leukemia CCRF-CEM cells. The performance of Compound 9 was evaluated against MTX. Four different types of cells were used: CCRF-CEM cells were unaltered; R30dm cells had a decreased amount of polyglutamate synthase; R1 cells had a twenty-fold increase in wild type DHFR protein and activity; and R2 cells were deficient in their ability to uptake the compounds into the cell. Results are presented in Table 5 below.

TABLE 5

Growth Inhibition of Parental CCRF-CEM and Sublines with Single, Defined Mechanisms of MTX Resistance During Continuous (0–120 hours) Exposure to MTX and Compound 311 ($EC_{50}$ in nM)

| Compound | CCRF-CEM | R30dm | R1 | R2 |
|---|---|---|---|---|
| MTX | 14.5 ± 0.4 (n = 5) | 14.5 ± 0.5 (n = 2) | 595 ± 5 (n = 2) | 3100 ± 100 (n = 2) |
| 311 | 12.8 ± 2.2 (n = 5) | 36 ± 1 (n = 2) | 515 ± 25 (n = 2) | 1650 ± 200 (n = 2) |

Average values are presented ± the standard deviation range for n=2 and ± the standard deviation range for n≧3.

As can be seen from the results of the above table, Compound 9 performed comparably to MTX. The example further demonstrates that polyglutamylation may play a limited role in the mechanism of action of Compound 9, even in continuous exposure. Both the R1 subline, with amplified DHFR expression, and the MTX-transport deficient R2 subline displayed resistance to MTX under continuous exposure.

Example 3

Compound 9 and MTX were also tested for growth inhibition of A253 and FaDu human squamous carcinoma cell lines; neither of these cell lines had any deficiencies. Results are presented below in Table 6.

TABLE 6

Growth Inhibition of A253 and FaDu Human Squamous Carcinoma Cell Lines Following Continuous (120 hours) Exposure to MTX and Compound 311 ($EC_{50}$ in nM)

| Compound | A253 | FaDu |
|---|---|---|
| MTX | 17 ± 1 | 31 ± 2 |
| 311 | 46 ± 4 | 22 ± 4 |

All values are average ± standard deviation range for duplicate determinations.

Example 4

Compound 9 and aminopterin were further tested for their activity as substrates for human leukemia cell CCRF-CEM folylpolyglutamate synthetase. Aminopterin is a classical 2,4-diamino antifolate substrate. Results are presented below in Table 7.

TABLE 7

Activity of Aminopterin and Compound 9 as Substrates for CCRF-CEM Human Leukemia Cell Folylpolyglutamate synthetase

| Substrate | $KM, \mu M$ | $V_{max,rel}$ | $V_{max}/K_{m(rel)}$ | n |
|---|---|---|---|---|
| Aminopterin | 4.3 ± 0.2 | 1 | 0.23 ± 0.01 | 3 |
| 9 | <1 | 0.72 ± 0.07 | >0.72 | 4 |

Values presented are average ± standard deviation.

This examples demonstrates that Compound 9 is a potent tumor cell growth inhibitor that shares determinates of response with MTX. It is similar in potency to MTX as an inhibitor of the growth of human leukemia and SCC cell lines in culture. DHFR is suggested as the target of Compound 9, which is supported by the data showing relatively potent DHFR inhibition in vitro and the cross-resistance to Compound 9 of a human cell line having amplified expression of DHFR. Compound 9 may also use the MTX/reduced folate-transport protein for uptake as evidenced by the cross-resistance of a human cell line in which this transport system is defective. This example indicates that Compound 9 may be an excellent substrate for human FPGS with a very low $K_m$. The slight cross-resistance to continuous exposure of the cell line having low levels of FPGS suggests that polyglutamate metabolites may play a role in growth inhibition even under these conditions.

Example 5

Compound 9 was further tested for its in vitro anti-cancer activity by the National Cancer Institute. Results are presented in Table 8 below. $GI_{50}$ represents the concentration at which growth was inhibited by 50%.

TABLE 8

In Vitro Anti-Cancer Activity of Compound 311

| Panel/Cell Line | $GI_{50}$ |
|---|---|
| Leukemia | |
| CCRF-CEM | ND |
| HL-60 (TB) | ND |
| MOLT-4 | ND |
| RPMI-8226 | ND |
| SR | >1.00E–04 |
| Non-Small Cell Lung Cancer | |
| A549/ATCC | <1.00E–08 |
| BKVX | 3.97E–05 |
| HOP-62 | <1.00E–08 |
| HOP-92 | 8.40E–06 |
| NCI-H226 | >1.00E–04 |
| NCI-H23 | 5.75E–08 |
| NCI-H322M | >1.00E–04 |
| NCI-H522 | >1.00E–04 |
| Colon Cancer | |
| COLO 205 | >1.00E–04 |
| HCC-2998 | <1.00E–08 |
| HCT-116 | <1.00E–08 |
| HCT-15 | <1.00E–08 |
| HT29 | <1.00E–08 |
| KM12 | 3.32E–05 |
| SW-620 | 3.15E–06 |
| CNS Cancer | |
| SF-268 | <1.00E–08 |
| SF-295 | <1.00E–08 |
| SF-539 | <1.00E–08 |
| SNB-19 | >1.00E–04 |
| SNB-75 | <1.00E–08 |
| U251 | <1.00E–08 |
| Melanoma | |
| LOX IMVI | <1.00E–08 |
| MALME-3M | <1.00E–08 |
| M14 | <1.00E–08 |
| SK-MEL-2 | >1.00E–04 |
| SK-MEL-28 | >1.00E–04 |
| UACC-257 | ND |
| UACC-62 | <1.00E–08 |
| Ovarian Cancer | |
| IGROV1 | <1.00E–08 |
| OVCAR-3 | >1.00E–04 |
| OVCAR-4 | >1.00E–04 |
| OVCAR-5 | >1.00E–04 |
| OVCAR-8 | <1.00E–08 |
| SK-OV-3 | >1.00E–04 |
| Renal Cancer | |
| 786-0 | <1.00E–08 |
| ACHN | <1.00E–08 |

TABLE 8-continued

In Vitro Anti-Cancer Activity of Compound 311

| Panel/Cell Line | GI$_{50}$ |
|---|---|
| CAKI-1 | <1.00E–08 |
| RXF 393 | >1.00E–04 |
| SN12C | <1.00E–08 |
| TK-10 | >1.00E–04 |
| UO-31 | <1.00E–08 |
| Prostate Cancer | |
| PC-3 | >1.00E–04 |
| DU-145 | 1.09E–08 |
| Breast Cancer | |
| MCF7 | <1.00E–08 |
| MCF7/ADR-RES | <1.00E–08 |
| MDA-MB-231/ATCC | >1.00E–04 |
| HS 578T | >1.00E–04 |
| MDA-MB-435 | 6.87E–07 |
| MDA-N | <1.00E–08 |
| BT-549 | >1.00E–04 |
| T-47D | >1.00E–04 |

As will be appreciated by one skilled in the art, the lower the GI$_{50}$, the more effective the compound. A GI$_{50}$ of less than $1.00 \times 10^{-8}$ indicates a very high potency, whereas a GI$_{50}$ greater than $1.00 \times 10^{-4}$ indicates that the compound was relatively inactive.

As demonstrated in Table 8 above, Compound 9 was shown to be highly selective against certain cell lines, with little or no activity against other cell lines. This result indicates that Compound 9 is not a general poison, but rather is very selective. For example, in the eight breast cancer cell lines, Compound 9 was found to be highly potent, with GI$_{50}$ of less than $1.00 \times 10^{-8}$M, against the MCF7, MCF7-ADR-RES (resistant cell line) and the MDA-N cell lines, but was relatively inactive, with GI$_{50}$ greater than $1.00 \times 10^{-4}$M against breast cancer cell lines MDA-MB-231/ATCC, HS578T, BT-549 and T-47D. The difference in activity of these two sets of breast cancer cells is ten thousand fold, which indicates a very high degree of selectivity. This kind of selectivity is repeated in all of the cell lines tested.

Example 6

The inhibitory concentration of Compounds 313 and 314 against TS was determined. The performance of these compounds was measured against PDDF, which is a standard TS inhibitor and experimental anticancer agent. The compounds were all tested against *Lactobacillus casei* and human lymphoma cells. Results are presented in Table 9 below:

TABLE 9

Inhibitory Concentrations (IC$_{50}$ in $\mu$M) Against TS

| Compound | L. Casei TS | Human TS |
|---|---|---|
| 313 | 180 | 180 |
| 314 | 360 | ND |
| PDDF | 0.036 | 0.036 |

As can be seen from the above table, Compound 313 and 314, when tested, had surprisingly high inhibitory concentration when compared with that of PDDF.

Example 7

Compounds 315 and 317–322 were tested for their inhibitory activity against TS. The performance of these compounds was measured against ZD1694, which is in Phase III clinical trials as an antitumor agent. All of the compounds were tested against human cells, *L. casei*, *E. coli*, and *S. faecium*. Results are presented in the Table 10 below.

TABLE 10

Inhibitory Concentrations (IC$_{50}$ in $\mu$M) Against TS

| Compound | Human | L. Casei | E. Coli | S. Faecium |
|---|---|---|---|---|
| ZD1694 | 0.22 | 8.8 | 5.3 | 8.8 |
| 315 | >25 | >26 | ND | ND |
| 317 | 2.4 | >24 (33%) | >24 (30%) | >24 (12%) |
| 318 | 0.13 | 45 | 45 | >45 (31%) |
| 319 | 1.0 | >26 (0%) | >26 (40%) | 30 |
| 320 | 0.15 | 5.1 | 13 | 15 |
| 321 | 30 | >30 (0%) | >30 (30%) | >30 (20%) |
| 322 | 2.0 | >25 (32%) | >25 (36%) | >25 (0%) |

Example 8

Compounds 317–320 were also tested for their ability to inhibit DHFR. Selectivity ratios were determined as measured against *Pneumocystis carinii* (Pc), *Toxoplasmosis gondii* (Tg) and rat liver (RL). Results are presented in Table 11 below.

TABLE 11

Inhibition of Dihydrofolate Reductase (IC$_{50}$ in $\mu$M)

| Compound | Pc | RL | Selectivity Ratio RL/Pc | Tg | Selectivity Ratio RL/Tg |
|---|---|---|---|---|---|
| 317 | >21 | >21 | ND | 20 | >1 |
| 318 | >20 | >20 | ND | 11.7 | >1.7 |
| 319 | 40 | 24.6 | 0.62 | 3.1 | 7.94 |
| 320 | >15 | 7470 | ND | 244 | 30.61 |

As can be seen from Table 11, Compound 320 is highly selective for *Toxoplasmosis gondii* DHFR.

Example 9

Compounds 317–322 were also tested for their ability to inhibit the growth of FaDu human squamous cell carcinoma cell lines. The performance of these compounds was tested against PDDF, and AG331, which is a TS inhibitor in Phase III clinical trials as an antitumor agent. Results are presented in Table 12 below.

TABLE 12

Growth Inhibition of the FaDu Human Squamous Cell Carcinoma Cell Line By Continuous (120 hours) Exposure to the Inhibitors

| Compound | EC$_{50}$ $\mu$M | n |
|---|---|---|
| 317 | >10 | 2 |
| 318 | insoluble | — |
| 319 | 6.7 ± 1.5 | 3 |
| 320 | 1.5 ± 0.4 | 3 |
| 321 | >10 | 2 |
| 322 | ND | — |
| PDDF | 1.7 ± 0.2 | 4 |
| AG331 | 1.0 ± 0.1 | 6 |

Values presented are average ± standard deviation.

Example 10

Figure 2:
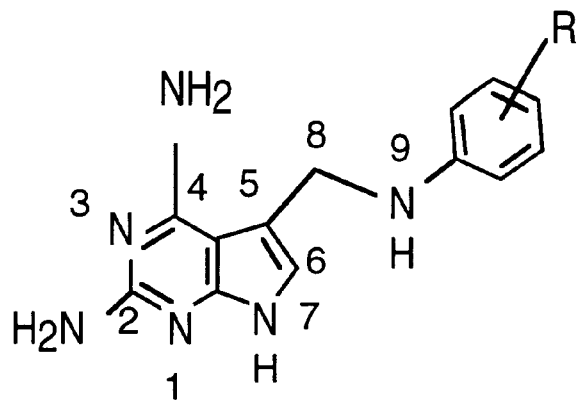
FIG. 2 shows compounds 1–9 as synthesized by the methods shown in FIG. 1.
Figure 2:
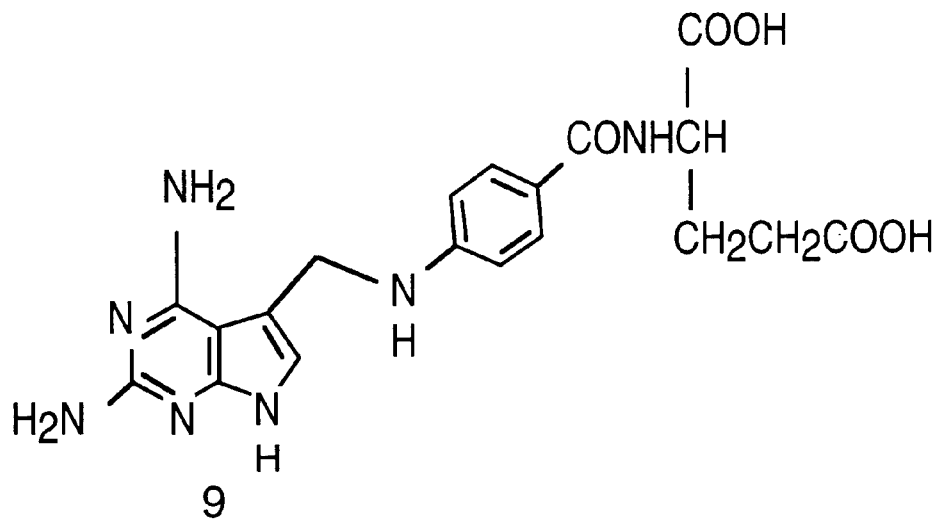
Figure 3:
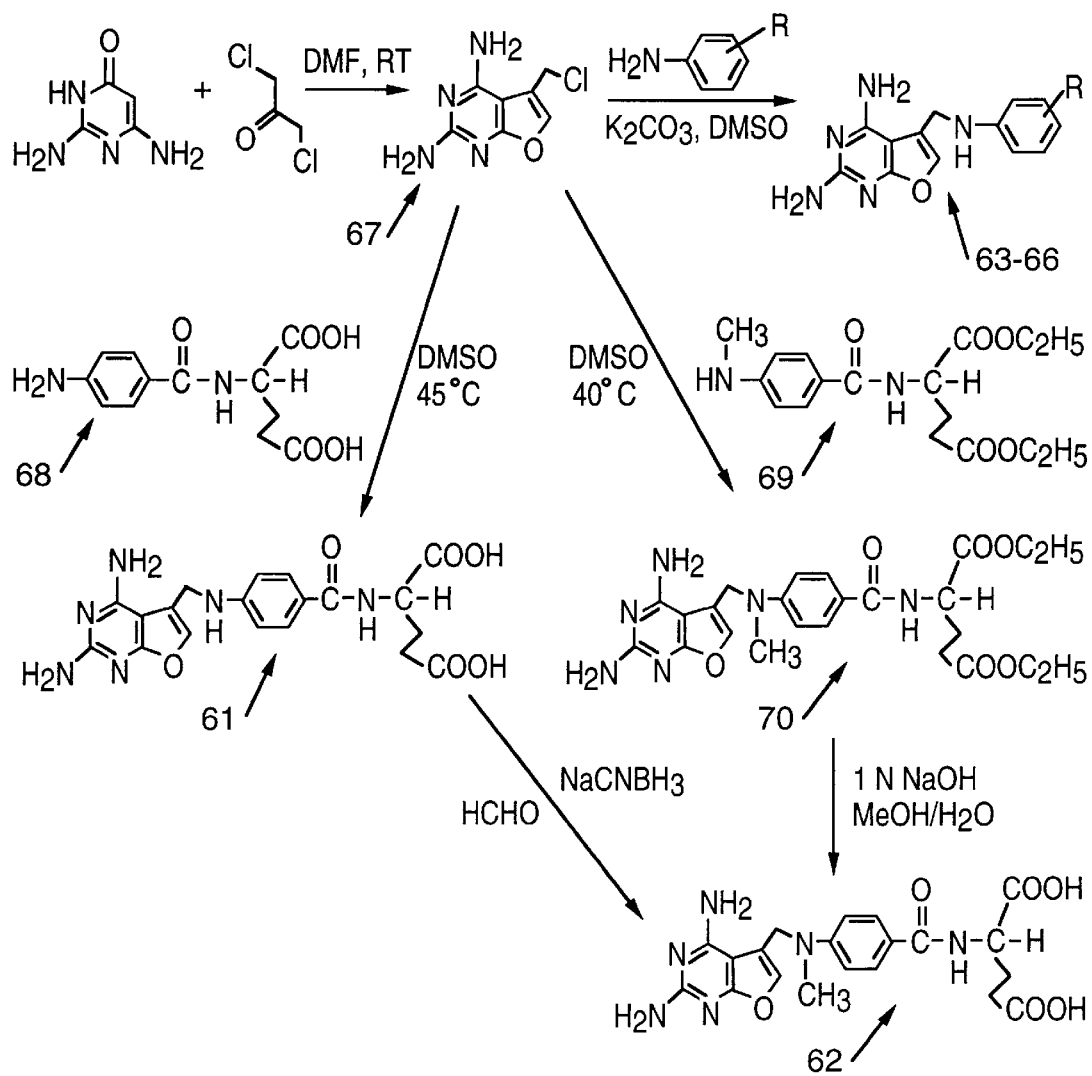
FIG. 3 shows a schematic diagram of the methods of preparing N-[4-[N-[2,4-diaminofuro[2,3-d]pyrimidin-5-yl]methyl]amino]benzoyl]-L-glutamic acid and the N-9 methyl analogue thereof.
Figure 4:
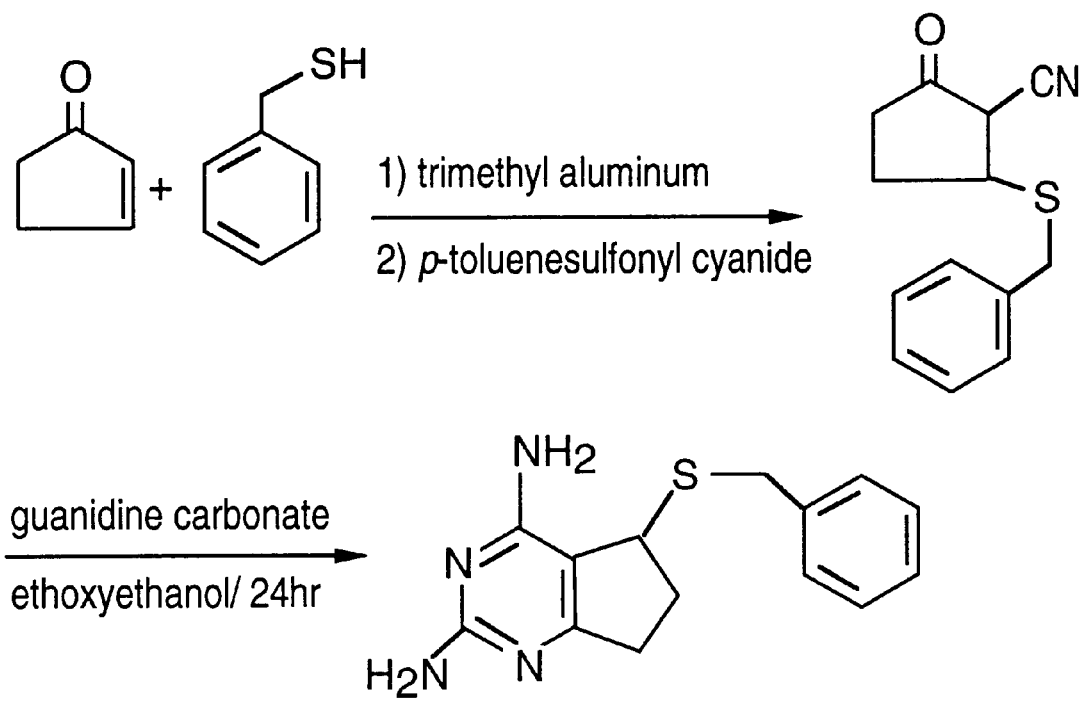
FIG. 4 shows a schematic diagram of the methods of preparing of a compound having formula 8.

The following example describes methods of synthesizing the compounds represented by formula 2. These methods are illustrated in FIG. 1. Reference numerals and letters correspond with those of FIGS. 1 and 2.

2-amino-3,4-dicyanopyrrole (11)

A mixture of about 4.0 grams (g) of Compound 10, about 4.0 g of 5% Pd on $BaCO_3$, about 15 milliliters (ml) of DMF and about 25 ml methanol was hydrogenated at about 50 psi for approximately 3 hours. The mixture was filtered through Celite®, a filtering composition commercially available from Johns-Mannville Products Corporation, and the filtrate concentrated under reduced pressure to about 10 ml. About 200 ml of cold water was added to the concentrate, and a light brown solid was formed. This solid was collected by filtration to yield about 1.60 g of Compound 11.

2,4-diamino-5-cyanopyrrolo[2,3-d]pyrimidine (12)

A mixture of about 2.63 g of Compound 11 and about 2.5 g of chlorformamidine hydrochloride in about 50 ml Dowtherm-A®, a liquid heat transfer media commercial available from Dow Chemical Company, was heated at between about 160° and 170° C. for approximately 48 hours, until Compound 11 could not be detected by thin layer chromatography (TLC). The mixture was cooled to room temperature, and about 50 ml of $Et_2O$ was added thereto. A greenish-brown solid resulted. The solid was filtered and washed with $Et_2O$ to yield about 3.0 g of Compound 12.

2,4-diaminopyrrolo[2,3-d]pyrimidine-5-carboxaldehyde (13)

About 6.0 g of Raney Ni was added to a stirred solution of about 2.0 g of Compound 12 and about 50 ml of HCOOH. The mixture was heated to about 80° C. for about 2 hours, until no starting material could be detected by TLC. The mixture was cooled to room temperature and filtered through Celite®. The filtrate was evaporated under reduced pressure, azeotroping with methanol to remove traces of HCOOH. The residue was dissolved in about 25 ml of hot water, treated with Norit®, an activated adsorption carbon commercially available from American Norit Company, Inc., and filtered through Celite®. The filtrate was neutralized with $NH_4OH$. The light brown precipitate which resulted was filtered and dried to yield about 1.40 g of Compound 13, which was immediately used in subsequent reactions without further purification.

2,4-diamino-5[[N-(3',4',5'-trimethoxyphenyl)imino]methyl]pyrrolo]2,3-d]pyrimidine (14a)

A solution containing about 1.30 g of Compound 12 and about 2.06 g of 3,4,5-trimethoxyaniline in about 75 ml of 70% acetic acid and containing about 6.50 g of damp Raney Ni was hydrogenated at atmospheric pressure for about 24 hours at room temperature. The mixture was treated with Norit® and filtered through Celite® and the solvent removed from the filtrate by evaporation under reduced pressure. About 15 ml of cold water was added to the residue, and the suspension was added to about 100 ml of a stirred, cold, saturated solution of $NaHCO_3$. The mixture was stirred for about 10 minutes and refrigerated for about 6 hours. The brown precipitate which formed was collected, washed with water, and dried. This product, containing Compound 14A, was washed repeatedly with $Et_2O$ until no aniline was detected by TLC in the washings. The residue was then dissolved in about 100 ml methanol and filtered, and the filtrate evaporated under reduced pressure to near dryness. About 50 ml $Et_2O$ was added to the solution, and the precipitate filtered to yield about 1.20 g of Compound 15a.

2,4-diamino-5-[(3',4',5'-trimethoxyanilino)methyl]pyrrolo[2,3-d]pyrimidine(1)

About 0.05 g $NaCNBH_3$ were added to a solution containing about 0.20 g of Compound 15a in about 25 ml methanol. The pH was adjusted to about 2 with a 50% methanol/hydrochloric acid solution. The mixture was continuously stirred at room temperature for about 4 hours. The solvent was evaporated to dryness, and cold water was added to the residue, which was neutralized with $NH_4OH$. The resulting precipitate was filtered, dried, and dissolved in a 9:1 mixture of $CHCl_3$/methanol. This was applied to a silica gel column (2.4 cm×20 cm) packed in $CHCl_3$. The column was eluted with a gradient of 1% methanol in $CHCl_3$ to 15% methanol in $CHCl_3$. Fractions corresponding to the product, as determined by TLC, were pooled and evaporated to dryness under reduced pressure. The residue was triturated in cold $Et_2O$ and filtered to yield about 0.10 g of Compound 1.

2,4-diamino-5-[(3',4'-dimethoxyanilino)methyl]pyrrolo[2,3-d]pyrimidine(2)

The Schiff base was prepared as described for Compound 15a, except that the reaction was carried out in 80% acetic acid and using 3,4-dimethoxyaniline to yield about 1.20 g of Compound 15b. Reduction of Compound 15b was carried out as described for Compound 1. The crude product was dissolved in methanol and filtered. The filtrate was evaporated under reduced pressure to dryness. The residue was triturated in cold $Et_2O$ and filtered to yield about 0.51 g of Compound 2.

2,4-diamino-5-[(4'-methoxyanilino)methyl]pyrrolo[2,3-d]pyrimidine(3)

The Schiff base was prepared as described above for Compound 15b using 4-methoxyaniline to yield about 0.32 g of Compound 15c. Reduction of Compound 15c was carried out as described for Compound 15b to yield Compound 3.

2,4-diamino-5-[(2',5'-dimethoxyanilino)methyl]pyrrolo[2,3-d]pyrimidine(4)

The Schiff base was prepared as described above for Compound 15b using 2,5-dimethoxyaniline to yield about 0.90 g of Compound 15d. Reduction of Compound 15d was carried out as described above for Compound 15b to yield about 0.25 g of Compound 4.

2,4-diamino-5-[[(2',5'-diethoxyphenyl)imino]methyl]-pyrrolo[2,3-d]pyrimidine(15e)

Method A, starting from Compound 13: A solution of about 1.15 g of Compound 13 and about 1.76 g of 2,5-diethoxyaniline (14e) in about 75 ml 70% acetic acid containing about 5.75 g of damp Raney Ni was hydrogenated at about 55 psi for about 12 hours at room temperature. The mixture was filtered through Celite® and the filtrate evaporated under reduced pressure. About 15 ml cold water were added to the residue and this suspension was added to about 100 ml of a stirred, cold, saturated solution of $NaHCO_3$. The mixture was stirred for an additional 10 minutes and refrigerated for about 4 hours. The brown precipitate which resulted was collected, washed with water, and dried. The crude product containing Compound 14e was washed repeatedly with $Et_2O$ until no aniline could be detected by TLC in the washings. The residue was then dissolved in about 100 ml methanol and filtered, and the filtrate evaporated to dryness under reduced pressure. About 20 ml Et$_2$O was added to the solution, and the precipitate filtered to yield about 1.20 g of Compound 15e.

Method B, starting from Compound 12: The Schiff base was prepared as described above for Compound 15b using 2,5-diethoxyaniline to yield about 0.90 g of Compound 15e, which was identical in all respects with the sample prepared according to Method A described above.

2,4-diamino-5-[(2',5'-diethoxyanilino)methyl]pyrrolo [2,3-d]pyrimidine(5)

Reduction of Compound 15e was performed as described above for Compound 15b to yield about 0.36 g of Compound 5.

2,4-diamino-5-[(3',4'-dichloroanilino)methyl]pyrrolo [2,3-d]pyrimidine(6)

The Schiff base was prepared as described above for Compound 15b using 3,4-dichloroaniline to yield about 1.0 g of Compound 15f. Reduction of Compound 15f was performed as described above for Compound 15b to yield about 0.34 g of Compound 6.

2,4-diamino-5-[(1'-naphthylamino)methyl]pyrrolo[2, 3-d]pyrimidine(7)

The Schiff base was prepared as described above for Compound 15b, except that the reaction was carried out at about 30 psi for about 12 hours at room temperature using 1-aminonaphthylene to yield about 0.92 g of Compound 15g. Reduction of Compound 15g was carried out as described above for Compound 15b, except that glacial acetic acid was used to adjust the pH to about 2. Crude product 7 was dissolved in a 9:1 mixture of CHCl$_3$/methanol, which was loaded on a silica gel column (2.4 cm×20 cm) packed in CHCl$_3$. The column was eluted with a gradient of 1% methanol in CHCl$_3$ to 5% methanol in CHCl$_3$. Fractions corresponding to the product, as determined by TLC, were pooled and evaporated under reduced pressure to dryness. The residue was triturated in cold Et$_2$O and the suspension filtered to yield about 0.24 g of Compound 7.

2,4-diamino-5-(anilinomethyl)pyrrolo[2,3-d] pyrimidine(8)

The Schiff base was prepared as described above for Compound 15b using aniline to yield about 0.69 g of Compound 15h. Reduction of Compound 15h was carried out as described for Compound 15b, except that glacial acetic acid was used to adjust the pH to about 2. About 0.19 g of Compound 8 resulted.

N-[4-[N-](2,4-diaminopyrrolo[2,3-d]pyrimidin-5-yl) methyl]amino]benzoyl]-L-glutamic acid (9)

The Schiff base was prepared as described above for Compound 15b using diethyl(p-aminobenzoyl)-L-glutamate to yield about 1.39 g of the diethylester of Compound 16. Reduction of Compound 16 was carried out as described above for Compound 15b to yield about 0.44 g of Compound 17. Hydrolysis of the esters was carried out by stirring a solution of about 0.30 g Compound 17 in about 10 ml of 1N sodium hydroxide and 10 ml methanol for about 72 hours at room temperature. The solvent was evaporated to 5 ml, and the mixture was carefully acidified with glacial acetic acid in an ice bath. The tan precipitate which resulted was filtered, washed with water, and dried to yield about 0.23 g of Compound 9.

Example 11

The DHFR inhibitory concentrations of Compounds 159–169, 171, 172, 175, 177, 178, and 179 was determined. Performance of these compounds was measured against TMQ and TMP. Inhibitory concentration was measured against *Pneumocystis carinii* and *Toxoplasmosis gondii*, as well as rat liver. Results are presented in Table 13 below.

TABLE 13

Inhibitory Concentrations (IC$_{50}$, μM) and Selectivity Ratios of 5-substituted furo[2,3-d]pyrimidines

| Compound # | Pc DHFR | RL DHFR | Selectivity Ratio RL/Pc | Tg DHFR | Selectivity Ratio RL/Tg |
|---|---|---|---|---|---|
| 159 | >26 | 252 | ND | >26 | ND |
| 160 | 19 | 23 | 1.2 | 19 | 1.2 |
| 161 | 0.65 | 12.3 | 18.9 | 11.6 | 1.1 |
| 162 | 13.5 | 12 | 0.89 | 37 | 0.32 |
| 163 | 41 | 36.5 | 0.89 | 38 | 0.96 |
| 164 | 14 | 60.3 | 4.31 | >42 | ND |
| 165 | >12 | >12 | ND | >12 | ND |
| 166 | 8.1 | 16.2 | 2.00 | 32.4 | 0.50 |
| 167 | 7.7 | 187 | 17.79 | 45.4 | 3.02 |
| 169 | 50.9 | 71.9 | 1.4 | >47 | ND |
| 171 | 44.8 | >27 | ND | >27 | ND |
| 172 | 284 | 34.3 | 0.1 | 21.5 | 1.6 |
| 175 | >31.3 | >31.3 | ND | >31.3 | ND |
| 177 | 8.6 | >83 | >10 | >83 | ND |
| 178 | >12 | >12 | ND | >12 | ND |
| 179 | >27.9 | >27.9 | ND | >27.9 | ND |
| TMQ | 0.042 | >0.003 | 0.07 | 0.01 | 0.30 |
| TMP | 12 | 133 | 11.1 | 2.7 | 49.0 |

As can be seen from the above table, Compound 161 is approximately 18 times more active than TMP and 1.7 times more selective; Compound 161 is 271 times more selective than TMQ and only 15 times less potent. These compounds, therefore, exhibit high selectivity for Pc DHFR. Compound 167 was also more selective than the compounds known in the art.

Example 12

Figure 6:
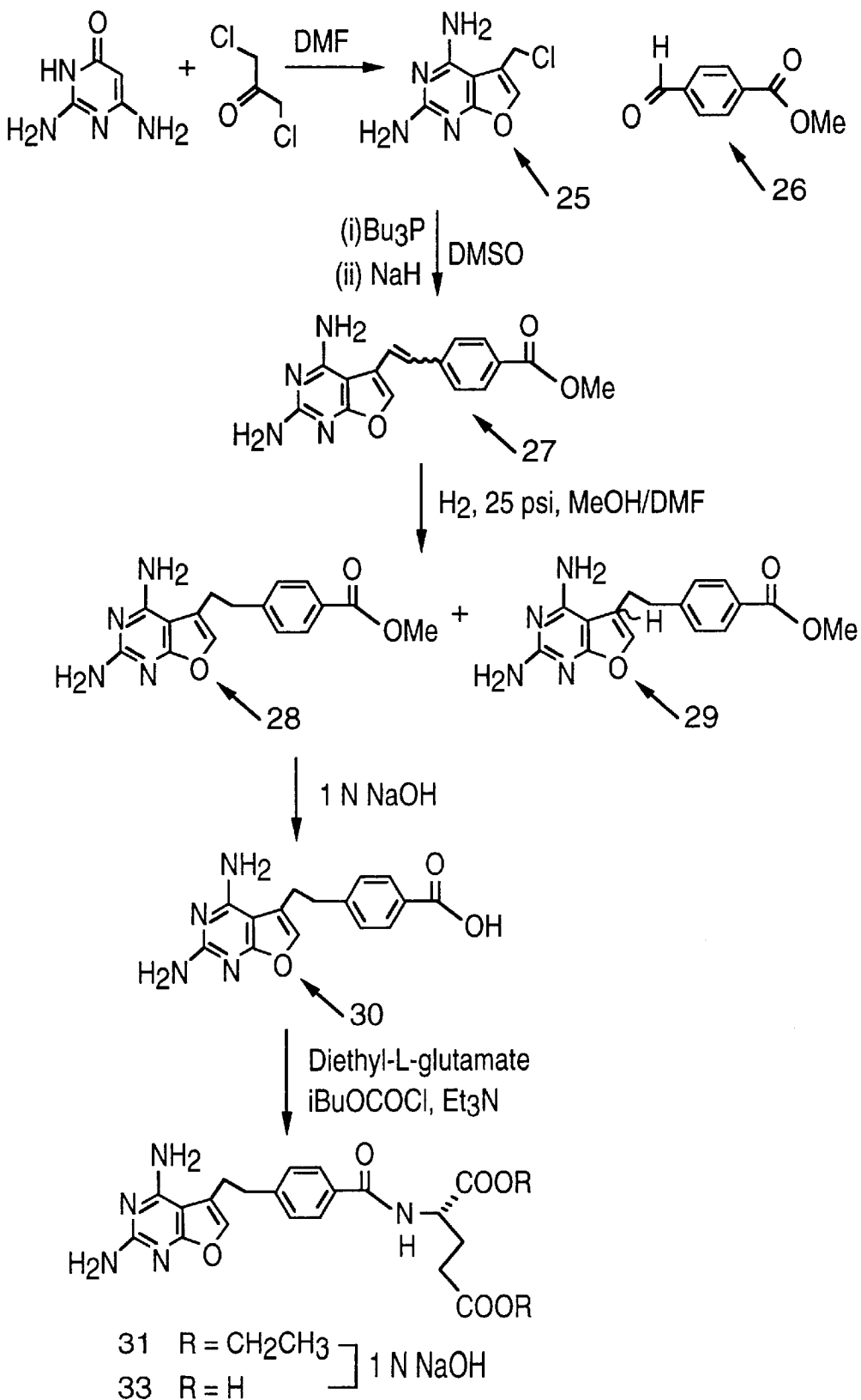
FIG. 6 shows a schematic diagram of the methods of preparing two of compounds having formula 4.
Figure 7:
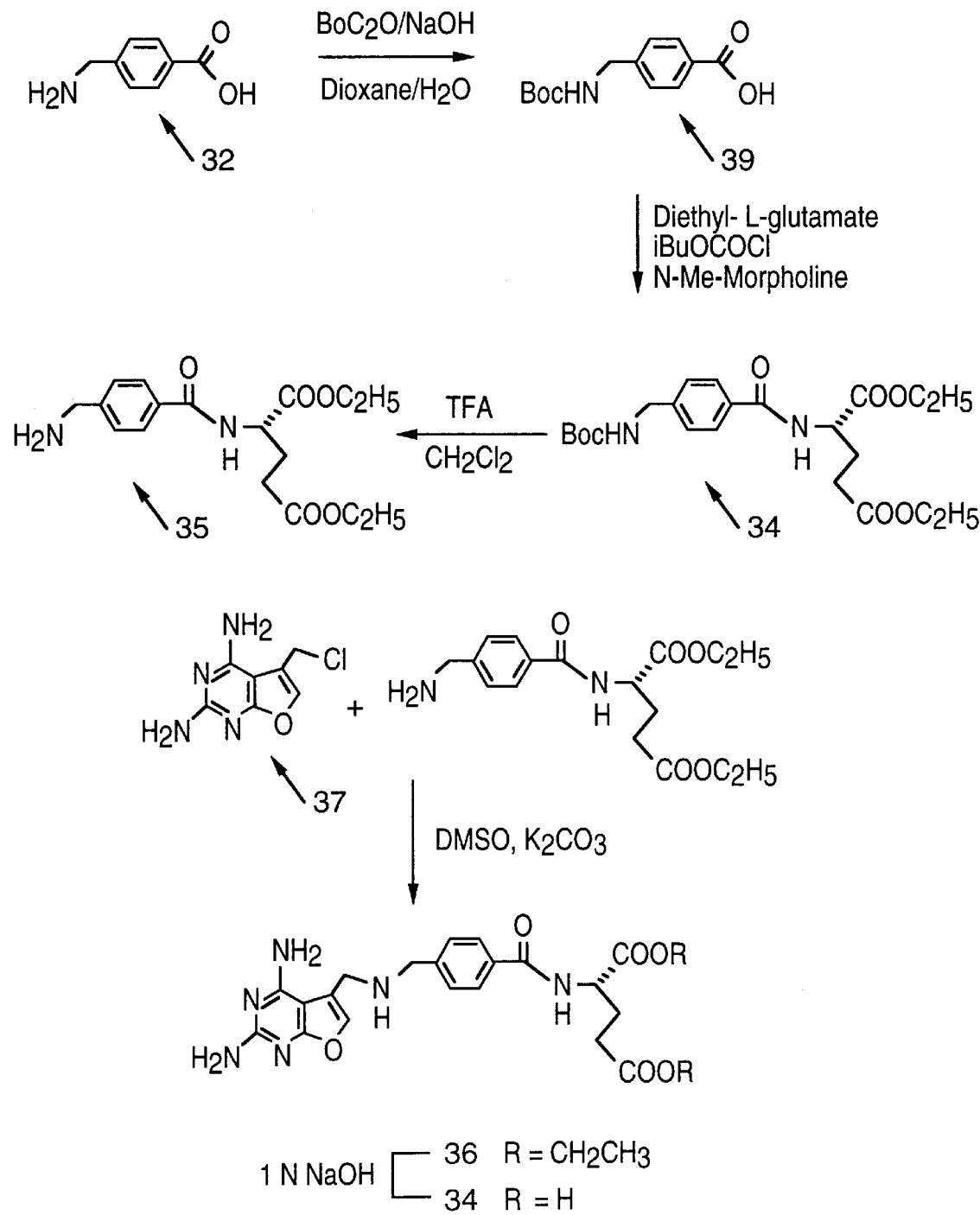
FIG. 7 shows a schematic diagram of the methods of preparing two of compounds having formula 4.
Figure 8:
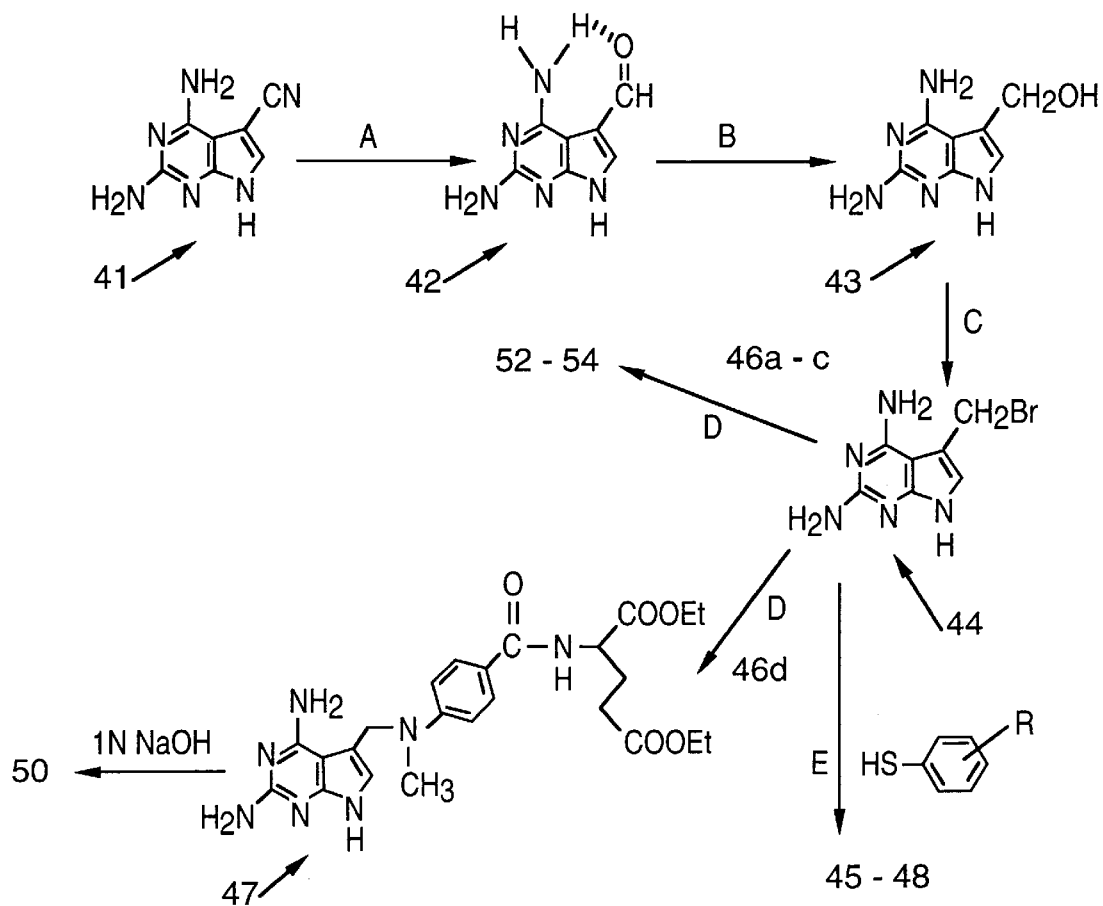
FIG. 8 shows a schematic diagram of the methods of preparing compounds having formula 9.
Figure 9:
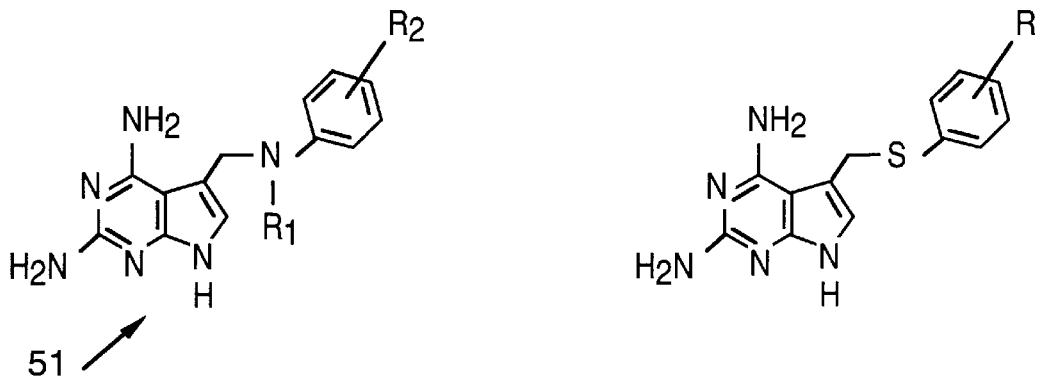
FIG. 9 shows of compounds having formula 9 as synthesized by the methods shown in FIG. 8.
Figure 9:
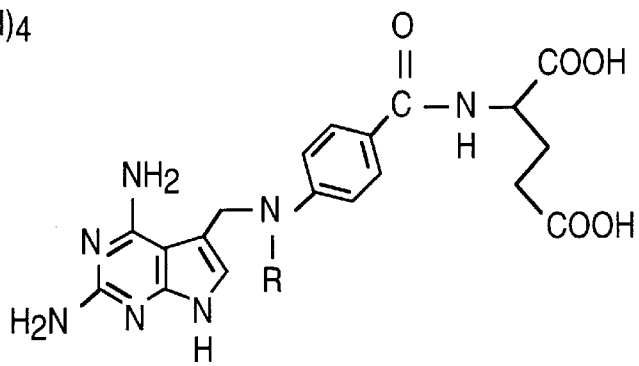

The following example provides methods for synthesizing compounds of formula 4. Reference numerals correspond with those in FIGS. 6 and 7.

Methyl 4-[2-(2,4-diaminofuro[2,3-d]pyrimidin-5-yl)-ethanyl]benzoate(27)

About 2.64 g of tributylphosphine was added to a solution containing about 0.79 g of 2,4-diamino-5(chloromethyl)furo [2,3-d]pyrimidine (25) in about 10 ml anhydrous DMSO. The mixture was stirred at about 60° C. for about 2 hours under nitrogen to form the phosphonium salt. The solution was cooled to room temperature, at which time 0.35 g of sodium hydride (60% dispersion in mineral oil) followed by about 0.72 g of methyl 4-formylbenzoate (26) was added. The mixture was stirred for about 24 hours at room temperature. The DMSO was removed by vacuum distillation. About 50 ml of ethylether was added to the residue and the supernatant decanted after 10 minutes. About 50 ml of ethylether was added again, the residue stirred for about 1 hour, and the supernatant decanted. This process was repeated 3 more times; the mixture was then stored at 0° C. with about 50 ml ethylether. After about 18 hours, the mixture was ultrasonicated for 2 hours and cooled to 0° C. for a period of about 10 hours. The resulting solid was filtered, washed with ethylether, air dried, washed with water and air dried again. The solid was then suspended in about 250 ml of hot methanol. About 3 g of silica gel were added to the filtrate, and the suspension was evaporated to dryness under reduced pressure. The silica gel plug was loaded on a dry silica gel column (2.4×20 cm) and flushed initially with CHCl$_3$ (500 ml). The column was then eluted sequentially with 100 ml portions of 1% to 8% methanol in CHCl$_3$. Fractions which showed a major spot at R$_f$ 0.66, as determined by TLC, were pooled and evaporated to dryness. The resulting residue was dissolved in glacial acetic acid and evaporated to dryness. This residue was redissolved in hot methanol and the solution stored at 0° C. for about 72 hours. The resulting solid was filtered, washed with ether, and dried to yield about 0.52 g of Compound 27.

Methyl 4-[2-(2,4-diaminofuro[2,3-d]pyrimidin-5-yl) ethyl]benzoate(28) and (+)-methyl 4-]2-(2,4-diamino-5,6-dihydrofuro[2,3-d]pyrimidin-5-yl)ethyl] benzoate(29)

About 0.31 g of 5% palladium on carbon was added to a solution containing about 0.155 g of Compound 27 in about 20 ml of a 1:1 mixture of methanol/DMF. The suspension was hydrogenated in a Parr apparatus at room temperature and 25 psi of hydrogen pressure for 30 minutes. The reaction mixture was filtered through Celite®, and the catalyst was washed with about 30 ml of a 1:1 methanol/DMF mixture. The filtrate was evaporated to dryness under reduced pressure, and the residue dissolved in about 100 ml methanol. About 500 mg of silica gel was added to the solution, and evaporated to dryness. The silica gel plug was loaded on a dry silica gel column (2.4×16 cm) and flushed with about 500 ml CHCl$_3$. The column was then eluted with a gradient of 1–9% methanol in CHCl$_3$, collecting 15 ml fractions. Fractions showing a single spot at R$_f$ 0.63, as determined by TLC, were pooled and evaporated to dryness, and the residue was stirred in ether, filtered, and dried to yield about 0.08 g of Compound 28. Later fractions from the column described above, showing a single spot at R$_f$ 0.52, were pooled and evaporated to dryness under reduced pressure, and the residue obtained was stirred in ether, filtered, and dried to yield about 0.02 g of Compound 29.

4-[2-(2,4-diaminofuro[2,3-d]pyrimidin-5-yl)ethyl] benzoic acid(30)

About 1.5 ml of 1N sodium hydroxide was added to a solution containing about 0.065 g of Compound 28 in about 10 ml of a mixture of 2:1 methanol/DMSO. The mixture was stirred at room temperature for 18 hours and evaporated to dryness under reduced pressure (oil pump). The residue was dissolved in about 5 ml water and 1N HCl was added dropwise to bring the pH of the solution to 5.5. The suspension was cooled to 5° C. for about 12 hours and filtered. The residue was washed sequentially with water, acetone and ether and dried to yield about 0.05 g of Compound 30.

N-[4-[2-(2,4-diaminofuro[2,3-d]pyrimidin-5-yl) ethyl]-benzoyl]-L-glutamic acid (33)

About 45 microliters of triethylamine was added to a suspension containing about 0.047 g of Compound 30 in about 3 ml anhydrous DMF, and the mixture stirred under nitrogen at room temperature for about 5 minutes. The solution was cooled to 0° C., about 42 microliters of isobutylchloroformate was added, and the mixture stirred at 0° C. for 30 minutes. About 0.077 g of diethyl-L-glutamate hydrochloride was added to the reaction mixture, followed immediately by about 45 microliters triethylamine. The mixture was slowly allowed to warm to room temperature, and stirred under nitrogen for a period of about 18 hours. The reaction mixture was then subjected to another cycle of activation using ½ of the quantities listed above. The reaction mixture was warmed to room temperature and stirred for 24 hours and evaporated to dryness under reduced pressure. The residue was dissolved in a 4:1 mixture of CHCl$_3$/methanol and chromatographed on a silica gel column (2.4×15 cm), packed with CHCl$_3$/methanol (24:1), eluting with 24:1 CHCl$_3$/methanol. Fractions showing a single spot were pooled and evaporated to dryness. The residue was stirred in cold anhydrous ether and filtered to obtain about 0.054 g of Compound 31. About 1 ml of 1N sodium hydroxide was added to a solution containing about 0.052 g of Compound 31 in about 5 ml methanol and the solution stirred at room temperature for 24 hours. The methanol was evaporated under reduced pressure, the residue dissolved in about 5 ml water, and stirring was continued for an additional 24 hours. The pH of the solution was then adjusted to 4.0 by dropwise addition of 1N HCl. The resulting suspension was stored at 5° C. for about 12 hours and filtered; the residue was washed well with water and acetone and dried to yield about 0.044 g of Compound 33.

4-[[N-(tert-butyloxycarbonyl)amino]methyl]benzoic acid (39)

About 10 ml of 1N sodium hydroxide was added to a solution containing about 1.51 g of 4-(aminomethyl)benzoic acid (32) in about 20 ml of 1:1 dioxane/water. The mixture was stirred at room temperature for about 12 hours, and evaporated to half of its original volume under reduced pressure. The pH of the solution was adjusted to 3 by dropwise addition of 50% aqueous HCl, while maintaining the temperature below 10° C. with an ice bath. The resulting suspension was diluted with water (70 ml) and extracted with ethylacetate (3×50 ml). The combined organic layers were washed with about 50 ml saturated NaCl, dried MgSO$_4$, and filtered. The filtrate was evaporated to dryness under reduced pressure and the residue recrystallized from a mixture of ethylacetate/hexanes to yield about 2.10 g of Compound 39.

Diethyl-N-[4-[[N-(tert-butyloxycarbonyl)amino] methyl]benzoyl]-L-glutamate(34)

A solution containing about 1.26 g of Compound 39 in about 20 ml anhydrous DMF under nitrogen was cooled in an ice-salt bath. About 0.55 ml of N-methylmorpholin was added to the cooled solution, followed 5 minutes later by about 0.65 ml isobutylchloroformate. After stirring for a period of about 20 minutes, 1.20 g diethyl-L-glutamate hydrochloride was added, followed immediately by about 0.55 ml N-methylmorpholin. The reaction mixture was warmed to room temperature and stirred for 12 hours. At this time, the activation cycle was repeated using ½ the amounts of reagents indicated above, after which the reaction mixture was warmed to room temperature and stirred for an additional 12 hours. The solvents were removed under reduced pressure, and the residue was dissolved in about 100 ml CH$_2$Cl$_2$, washed with about 75 ml water, 50 ml 0.1 NHCl, and about 50 ml saturated NaCl. The organic layers were dried (MgSO$_4$) and filtered. The filtrate was evaporated under reduced pressure and the residue was flash chromatographed on silica gel (2.4×24 cm), eluting first with CH$_2$Cl$_2$ and then with 1% methanol in CH$_2$Cl$_2$. Fractions showing a single spot corresponding to the product were pooled and evaporated under reduced pressure to yield about 1.29 g of Compound 34.

Diethyl N-[4-(aminomethyl)benzoyl]-L-glutamate (35)

About 1.8 ml trifluoroacetic acid was added dropwise to a stirred solution containing about 1.0 g of Compound 34 in about 20 ml $CH_2Cl_2$. The mixture was stirred at room temperature for 15 minutes, evaporated to dryness under reduced pressure, and co-evaporated twice with about 30 ml absolute ethanol. The residue was then subjected to column chromatography on silica gel (1.5×15 cm), eluting with a gradient of 5–10% methanol in $CHCl_3$ to yield about 0.68 g of Compound 35.

Diethyl N-[4-[N-](2,4-diaminofuro[2,3-d]pyrimidin-5-yl)methyl(amino)methylbenzoyl)-L-glutamate (37)

About 0.28 g of anhydrous $K_2CO_3$ and about 0.67 g of Compound 35 were added to a solution containing about 0.2 g of Compound 35 in about 3 ml anhydrous DMSO. The reaction mixture was stirred under nitrogen at room temperature for 24 hours. The temperature was then raised to about 45° C. and the reaction continued for an additional 48 hours. The reaction mixture was then cooled to room temperature, diluted with about 50 ml water and stirred for about 8 hours. The solid that separated was filtered, washed with water, air dried, and dissolved in methanol. About 1 g of silica gel was added to the solution and the suspension evaporated to dryness under reduced pressure. The silica plug was loaded on a dry silica gel column (2.4×17 cm) and eluted with a gradient of 1–7% methanol in $CHCl_3$. Fractions corresponding to the product were pooled and evaporated to dryness. The residue was triturated with cold anhydrous ether to yield about 0.25 g of Compound 37.

N-[4-[[N-](2,4-diaminofuro[2,3-d]pyrimidin-5-yl)methyl]amino]methyl]benzoyl]-L-glutamic acid (34)

About 1 ml of 1N sodium hydroxide was added to a solution containing about 0.1 g of Compound 37 in about 10 ml of 2:1 methanol/THF. The mixture was stirred at room temperature for about 24 hours. The volatiles were removed under reduced pressure, and the residue dissolved in about 5 ml water and stirred for an additional 24 hours. The solution was cooled in an ice bath and the pH adjusted carefully to 4.0 by dropwise addition of 1N HCl. The precipitate was collected by filtration, washed well with water and ether, and immediately dried under high vacuum to yield about 0.08 g of Compound 34.

Example 13

Compounds 33 and 34 were evaluated as inhibitors of *Lactobacillus casei* DHFR, human recombinant (REC) DHFR and DHFR isolated from human CCRP-CEM leukemic cells. The performance of these compounds was compared with that of MTX. The compounds were also evaluated as inhibitors of *L. casei* TS and human recombinant TS. The results are presented in Table 14 below.

TABLE 14

| | Inhibitory Concentrations ($IC_{50}$ in $\mu M$) | | | | |
|---|---|---|---|---|---|
| Compound | Human REC DHFR | L. casei DHFR | CCRF-CEM DHFR | Human REC TS | L. casei TS |
| 33 | 1.0 | 0.1 | 0.25 | 220 | 200 |
| 34 | >200 | >200 | 30.5 | 63.0 | >200 |
| MTX | 0.004 | 0.006 | 0.0007 | 170 | ND |

Example 14

Compounds 33 and 34 were also evaluated for their substrate activity in CCRF-CEM human leukemia folylpolyglutamate synthetase; the compounds were compared against aminopterin. Results are presented in Table 15 below.

TABLE 15

Substrate Activity of Compounds 33 and 34 for CCRF-CEM Human Leukemia Cell Folylpolyglutamate Synthetase

| Substrate | $K_m$, $\mu M$ | $V_{max(rel)}$ | $V_{max}/K_{m(rel)}$ |
|---|---|---|---|
| Aminopterin | 4.8 ± 0.7 (N = 6) | 1 (N = 6) | 0.21 ± 0.04 (N = 6) |
| 33 | 8.5 ± 2.1 (N = 3) | 0.65 ± 0.01 (N = 3) | 0.07 ± 0.02 (N = 3) |
| 34 | ND | 0.6 (N = 5) | ND |

Example 15

Compounds 33 and 34 were also tested for their growth inhibition of human T-lymphoblastic leukemia cell line CCRF-CEM, its MTX-resistance subline (R30dm), and human squamous cell carcinoma cell lines (FaDu and A235). The performance of these compounds was evaluated against MTX. Results are presented in Table 16 below.

TABLE 16

| | Growth Inhibition ($EC_{50}$, $\mu M$) During Continuous Exposure (0 to 120 hours) | | | |
|---|---|---|---|---|
| Compound | CCRF-CEM | R30DM | FaDu | A253 |
| 33 | 0.29 ± 0.01 (N = 3) | 4.25 ± 0.05 (N = 2) | 0.018 ± 0.02 (N = 2) | 0.54 ± 0.09 (N = 3) |
| 34 | 48.0 ± 23.0 (N = 2) | ND | ND | ND |
| MTX | 0.014 ± 0.001 (N = 10) | 0.018 ± 0.003 (N = 5) | 0.017 ± 0.002 (N = 5) | 0.013 ± 0.0008 (N = 3) |

Average values are presented ± range for N=2 and ± standard deviation for N≧3.

It will be appreciated by those skilled in the art that the present invention provides compounds, and pharmaceutically acceptable salts thereof, effective against infections caused by *Pneumocystis carinii* and *Toxoplasmosis gondii*, methods of preparing these compounds, and methods of using these compounds in a patient for therapeutic or prophylactic purposes. It will be further appreciated by those skilled in the art that this invention provides compounds, and pharmaceutically acceptable salts thereof, effective in reducing tumors or otherwise destroying cancerous cells in patients with cancer, methods of preparing these compounds, and methods of using these compounds in a patient for therapeutic purposes.

Whereas particular embodiments of this invention have been described above for purposes of illustration, it will be evident to those skilled in the art that numerous variations of the details of the present invention may be made without departing from the invention as defined in the appended claims.

What is claimed is:

1. A compound, and pharmaceutically acceptable salts thereof, having the formula:

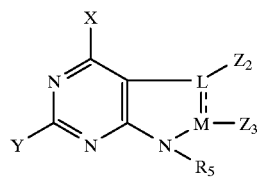

(1)

wherein X and Y are the same or different and are selected from the group consisting of OH and $NH_2$;

wherein L and M are selected from the group consisting of carbon and CH, the chemical bond between L and M is selected from the group consisting of a single bond and a double bond, L and M are carbon when the bond is a double bond, and L and M are CH when the bond is a single bond;

wherein $Z_2$ and $Z_3$ are different and are selected from the group consisting of $R_4$ and

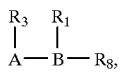

where $Z_2$ is $R_4$ when $Z_3$ is

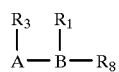

and $Z_2$ is

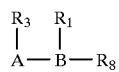

when $Z_3$ is $R_4$;

wherein A is selected from the group consisting of CH and zero;

wherein B is selected from the group consisting of CH, nitrogen, N—$CH_2$, $CH_2$—N, $CH_2$—$CH_2$, oxygen and sulfur, but B is not N—$CH_2$ when A is CH and $Z_3$ is $R_4$;

wherein A is not zero when B is $CH_2$—$CH_2$ and $Z_3$ is $R_4$;

wherein $R_1$ is selected from the group consisting of hydrogen, a lower alkyl group, a nitroso group, a formyl group and zero and $R_1$ is zero when B is oxygen or sulfur;

wherein $R_3$ is selected from the group consisting of hydrogen, a lower alkyl group and zero when $Z_2$ is $R_4$, and $R_3$ is selected from the group consisting of a lower alkyl group and zero when $Z_3$ is $R_4$, and $R_3$ is zero when A is zero;

wherein $R_4$ is selected from the group consisting of hydrogen and a lower alkyl group;

wherein $R_5$ is selected from the group consisting of hydrogen and a lower alkyl group;

wherein $R_8$ is selected from the group consisting of naphthyl, mono-, di- and tri-substituted naphthyl, thionaphthyl, thiophenyl and hydroxyphenyl when $R_1$ is hydrogen and $R_4$ is hydrogen;

wherein $R_8$ is selected from the group consisting of phenyl, mono-, di- and tri-substituted phenyl, naphthyl, mono-, di- and tri-substituted naphthyl, pyridine and p-aroyl-L-glutamate when $R_1$ is a lower alkyl group and $R_4$ is hydrogen;

wherein $R_8$ is selected from the group consisting of pyridine, phenyl, mono-, di- and tri-substituted phenyl, naphthyl, and mono-, di- and tri-substituted naphthyl and p-aroyl-L-glutamate when $R_1$ is zero;

wherein $R_8$ is selected from the group consisting of phenyl, mono-, di- and tri-substituted phenyl, naphthyl, mono-, di- and tri-substituted naphthyl and p-aroyl-L-glutamate when $R_1$ is hydrogen and $R_4$ is a lower alkyl group; and wherein $R_8$ is not p-benzoyl-L-glutamate or pyridine when X is OH, A is zero, B is sulfur, $R_4$ is methyl and $R_5$ is hydrogen, and $R_8$ is not p-benzoyl-L-glutamate when X is OH, A is CH, B is CH, $R_4$ is hydrogen and $R_5$ is hydrogen; and wherein each lower alkyl group is independently selected from the group consisting of lower alkyl groups having from 1 to 6 carbons.

2. The compound, and pharmaceutically acceptable salts thereof, of claim 1, wherein X is $NH_2$, Y is $NH_2$, the bond between L and M is a double bond, A is CH, B is nitrogen, $R_1$ is hydrogen, $R_3$ is hydrogen, $R_4$ is hydrogen, $R_5$ is hydrogen and $R_8$ is selected from the group consisting of 1-naphthyl and 4-hydroxyphenyl.

3. The compound, and pharmaceutically acceptable salts thereof, of claim 1, wherein X is $NH_2$, Y is $NH_2$, the bond between L and M is a double bond, A is CH, B is nitrogen, $R_1$ is methyl, $R_3$ is hydrogen, $R_4$ is hydrogen, $R_5$ is hydrogen and $R_8$ is selected from the group consisting of 2,5-dimethoxyphenyl, 3,4-dichlorophenyl and 1-naphthyl.

4. The compound, and pharmaceutically acceptable salts thereof, of claim 1, wherein X is $NH_2$, Y is $NH_2$, the bond between L and M is a double bond, A is CH, B is sulfur, $R_1$ is zero, $R_3$ is hydrogen, $R_4$ is hydrogen, $R_5$ is hydrogen and $R_8$ is selected from the group consisting of 3,4-dimethoxyphenyl, 3,4-dichlorophenyl, 1-naphthyl and 2-naphthyl.

5. The compound, and pharmaceutically acceptable salts thereof, of claim 1, wherein X is $NH_2$, Y is $NH_2$, the bond between L and M is a double bond, A is CH, B is nitrogen, $R_1$ is methyl, $R_3$ is hydrogen, $R_4$ is hydrogen, $R_5$ is hydrogen and $R_8$ is p-benzoyl-L-glutamate.

6. The compound, and pharmaceutically acceptable salts thereof, of claim 1, wherein X is OH, Y is $NH_2$, the bond between L and M is a double bond, A is CH, B is nitrogen, $R_1$ is hydrogen, $R_3$ is hydrogen, $R_4$ is methyl, $R_5$ is hydrogen and $R_8$ is p-benzoyl-L-glutamate.

7. The compound, and pharmaceutically acceptable salts thereof, of claim 1, wherein X is OH, Y is $NH_2$, the bond between L and M is a double bond, A is CH, B is sulfur, $R_1$ is zero, $R_3$ is hydrogen, $R_4$ is methyl, $R_5$ is hydrogen and $R_8$ is 4-pyridine.

8. The compound, and pharmaceutically acceptable salts thereof, of claim 1, wherein X is OH, Y is $NH_2$, the bond between L and M is a double bond, A is zero, B is sulfur, $R_1$ is zero, $R_3$ is zero, $R_4$ is methyl, $R_5$ is hydrogen and $R_8$ is selected from the group consisting of 3,4-dimethoxyphenyl, 3,4-dichlorophenyl, 4-chlorophenyl, 4-NO2phenyl, phenyl and 2-naphthyl.

9. The compound, and pharmaceutically acceptable salts thereof, of claim 1, wherein X is OH, Y is $NH_2$, the bond between L and M is a double bond, A is CH, B is CH, $R_1$ is hydrogen, $R_4$ is hydrogen, $R_5$ is hydrogen and $R_8$ is selected from the group consisting of thiophenyl, 1-thionaphthyl and 2-thionaphthyl.

10. A method of therapeutically treating a patient for an illness comprising the steps of:

a) employing a compound, or pharmaceutically acceptable salts thereof, having the formula:

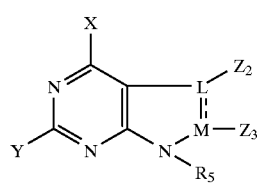

(1)

wherein X and Y are the same or different and are selected from the group consisting of OH and $NH_2$;

wherein L and M are selected from the group consisting of carbon and CH, the chemical bond between L and M is selected from the group consisting of a single bond and a double bond, L and M are carbon when the bond is a double bond, and L and M are CH when the bond is a single bond;

wherein $Z_2$ and $Z_3$ are different and are selected from the group consisting of $R_4$ and

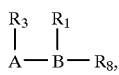

where $Z_2$ is $R_4$ when $Z_3$ is

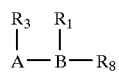

and $Z_2$ is

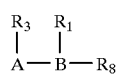

when $Z_3$ is $R_4$;

wherein A is selected from the group consisting of CH and zero;

wherein B is selected from the group consisting of CH, nitrogen, N—$CH_2$, $CH_2$—N, $CH_2$—$CH_2$, oxygen and sulfur, but B is not N—$CH_2$ when A is CH and $Z_3$ is $R_4$;

wherein A is not zero when B is $CH_2$—$CH_2$ and $Z_3$ is $R_4$;

wherein $R_1$ is selected from the group consisting of hydrogen, a lower alkyl group, a nitroso group, a formyl group and zero and $R_1$ is zero when B is oxygen or sulfur;

wherein $R_3$ is selected from the group consisting of hydrogen, a lower alkyl group and zero when $Z_2$ is $R_4$, and $R_3$ is selected from the group consisting of a lower alkyl group and zero when $Z_3$ is $R_4$, and $R_3$ is zero when A is zero;

wherein $R_4$ is selected from the group consisting of hydrogen and a lower alkyl group;

wherein $R_5$ is selected from the group consisting of hydrogen and a lower alkyl group;

wherein $R_8$ is selected from the group consisting of naphthyl, mono-, di- and tri-substituted naphthyl, thionaphthyl, thiophenyl and hydroxyphenyl when $R_1$ is hydrogen and $R_4$ is hydrogen;

wherein $R_8$ is selected from the group consisting of phenyl, mono-, di- and tri-substituted phenyl, naphthyl, mono-, di- and tri-substituted naphthyl, pyridine and p-aroyl-L-glutamate when $R_1$ is a lower alkyl group and $R_4$ is hydrogen;

wherein $R_8$ is selected from the group consisting of pyridine phenyl, mono-, di- and tri-substituted phenyl, naphthyl, mono-, di- and tri-substituted naphthyl and p-aroyl-L-glutamate when $R_1$ is zero;

wherein $R_8$ is selected from the group consisting of phenyl, mono-, di- and tri-substituted phenyl, naphthyl, mono-, di- and tri-substituted naphthyl and p-aroyl-L-glutamate when $R_1$ is hydrogen and $R_4$ is a lower alkyl group; and wherein $R_8$ is not p-benzoyl-L-glutamate or pyridine when X is OH, A is zero, B is sulfur, $R_4$ is methyl and $R_5$ is hydrogen, and $R_8$ is not p-benzoyl-L-glutamate when X is OH, A is CH, B is CH, $R_4$ is hydrogen and $R_5$ is hydrogen; and wherein each lower alkyl group is independently selected from the group consisting of lower alkyl groups having from 1 to 6 carbons;

b) incorporating said compound in a suitable pharmaceutical carrier; and c) administering a therapeutically effective amount of said compound incorporated in said carrier to a patient.

11. The method of claim 10, wherein X is $NH_2$, Y is $NH_2$, the bond between L and M is a double bond, A is CH, B is nitrogen, $R_1$ is methyl, $R_3$ is hydrogen, $R_4$ is hydrogen, $R_5$ is hydrogen and $R_8$ is p-benzoyl-L-glutamate.

12. The method of claim 10, wherein X is $NH_2$, Y is $NH_2$, A is zero, B is sulfur, $R_1$ is zero, $R_3$ is zero, $R_4$ is hydrogen, $R_5$ is hydrogen and $R_8$ is phenyl.

13. The method of claim 10, wherein said illness is cancer.

14. The method of claim 10, wherein said illness is selected from the group consisting of infection caused by *Pneumocystis carinii* and *Toxoplasmosis gondii*.

15. The method of claim 10, wherein said carrier is selected from the group consisting of physiologic saline and 5% dextrose for injection.

16. The method of claim 10, including administering said compound incorporated in said carrier to a patient parenterally.

17. The method of claim 10, including administering said compound incorporated in said carrier to a patient orally.

18. The method of claim 10, including administering said compound incorporated in said carrier to a patient topically.

19. A method of prophylactically treating a patient for an illness comprising the steps of:

a) employing a compound, or pharmaceutically acceptable salts thereof, having the formula:

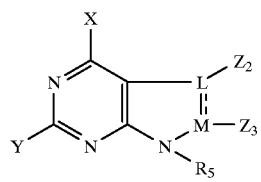

(1)

wherein X and Y are the same or different and are selected from the group consisting of OH and $NH_2$;

wherein L and M are selected from the group consisting of carbon and CH, the chemical bond between L and M is selected from the group consisting of a single bond and a double bond, L and M are carbon when the bond is a double bond, and L and M are CH when the bond is a single bond;

wherein $Z_2$ and $Z_3$ are different and are selected from the group consisting of $R_4$ and

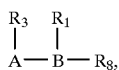

where $Z_2$ is $R_4$ when $Z_3$ is

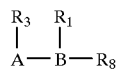

and $Z_2$ is

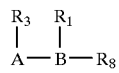

when $Z_3$ is $R_4$;

wherein A is selected from the group consisting of CH and zero;

wherein B is selected from the group consisting of CH, nitrogen, N—$CH_2$, $CH_2$—N, $CH_2$—$CH_2$, oxygen and sulfur, but B is not N—$CH_2$ when A is CH and $Z_3$ is $R_4$;

wherein A is not zero when B is $CH_2$—$CH_2$ and $Z_3$ is $R_4$;

wherein $R_1$ is selected from the group consisting of hydrogen, a lower alkyl group, a nitroso group, a formyl group and zero and $R_1$ is zero when B is oxygen or sulfur;

wherein $R_3$ is selected from the group consisting of hydrogen, a lower alkyl group and zero when $Z_2$ is $R_4$, and $R_3$ is selected from the group consisting of a lower alkyl group and zero when $Z_3$ is $R_4$, and $R_3$ is zero when A is zero;

wherein $R_4$ is selected from the group consisting of hydrogen and a lower alkyl group;

wherein $R_5$ is selected from the group consisting of hydrogen and a lower alkyl group;

wherein $R_8$ is selected from the group consisting of naphthyl, mono-, di- and tri-substituted naphthyl, thionaphthyl, thiophenyl and hydroxyphenyl when $R_1$ is hydrogen and $R_4$ is hydrogen;

wherein $R_8$ is selected from the group consisting of phenyl, mono-, di- and tri-substituted phenyl, naphthyl, mono-, di- and tri-substituted naphthyl, pyridine and p-aroyl-L-glutamate when $R_1$ is a lower alkyl group and $R_4$ is hydrogen;

wherein $R_8$ is selected from the group consisting of pyridine phenyl, mono-, di- and tri-substituted phenyl, naphthyl, mono-, di- and tri-substituted naphthyl and p-aroyl-L-glutamate when $R_1$ is zero;

wherein $R_8$ is selected from the group consisting of phenyl, mono-, di- and tri-substituted phenyl, naphthyl, mono-, di- and tri-substituted naphthyl and p-aroyl-L-glutamate when $R_1$ is hydrogen and $R_4$ is a lower alkyl group;

wherein $R_8$ is not p-benzoyl-L-glutamate or pyridine when X is OH, A is zero, B is sulfur, $R_4$ is methyl and $R_5$ is hydrogen, and $R_8$ is not p-benzoyl-L-glutamate when X is OH, A is CH, B is CH, $R_4$ is hydrogen and $R_5$ is hydrogen; and wherein each lower alkyl group is independently selected from the group consisting of lower alkyl groups having from 1 to 6 carbons;

b) incorporating said compound in a suitable pharmaceutical carrier; and c) administering a prophylactically effective amount of said compound incorporated in said carrier to a patient; wherein said illness is selected from the group consisting of infection caused by *Pneumocystis carinii* and *Toxoplasmosis gondii*.

20. The method of claim 19, wherein said carrier is selected from the group consisting of physiologic saline and 5% dextrose for injection.

21. The method of claim 19, including administering said compound incorporated in said carrier to a patient parenterally.

22. The method of claim 19, including administering said compound incorporated in said carrier to a patient orally.

23. The method of claim 19, including administering said compound incorporated in said carrier to a patient topically.

* * * * *

UNITED STATES PATENT AND TRADEMARK OFFICE
CERTIFICATE OF CORRECTION

PATENT NO. : 5,939,420
DATED : August 17, 1999
INVENTOR(S) : Aleem Gangjee

It is certified that error appears in the above-identified patent and that said Letters Patent is hereby corrected as shown below:

Column 12,
Line 58, "the group" should read -- Y are the --.

Column 26,
Line 7, remove the "X" at the end of line.

Column 32,
Line 31, "BKVX" should read -- EKVX --.

Column 35,
Line 3, "dicyanoplyrrole" should read -- dicyanopyrrole --.

Column 38,
Line 11, "Innibitory" should read -- Inhibitory --.

Column 41,
Line 20, "benzoyl)" should read -- (benzoyl) --.

Column 42,
Line 54, "N$\geq$" should read -- N$\geq$ --.

Signed and Sealed this

Sixteenth Day of October, 2001

Attest:

NICHOLAS P. GODICI
*Attesting Officer*  *Acting Director of the United States Patent and Trademark Office*